(12) United States Patent
Lee et al.

(10) Patent No.: US 10,932,483 B2
(45) Date of Patent: Mar. 2, 2021

(54) SWEETNESS ENHANCER

(71) Applicant: PepsiCo, Inc., Purchase, NY (US)

(72) Inventors: Thomas Lee, Scarsdale, NY (US); Gregory Yep, New Canaan, CT (US)

(73) Assignee: Pepsico, Inc., Purchase, NY (US)

( * ) Notice: Subject to any disclaimer, the term of this patent is extended or adjusted under 35 U.S.C. 154(b) by 516 days.

(21) Appl. No.: 15/509,817

(22) PCT Filed: Sep. 10, 2015

(86) PCT No.: PCT/US2015/049354
§ 371 (c)(1),
(2) Date: Mar. 8, 2017

(87) PCT Pub. No.: WO2016/040577
PCT Pub. Date: Mar. 17, 2016

(65) Prior Publication Data
US 2017/0245537 A1    Aug. 31, 2017

Related U.S. Application Data

(60) Provisional application No. 62/075,920, filed on Nov. 6, 2014, provisional application No. 62/049,057, filed on Sep. 11, 2014.

(51) Int. Cl.
| | |
|---|---|
| *A23L 27/30* | (2016.01) |
| *A23L 27/00* | (2016.01) |
| *A23L 2/60* | (2006.01) |
| *C07C 43/23* | (2006.01) |
| *A23L 7/143* | (2016.01) |
| *C07C 39/10* | (2006.01) |

(52) U.S. Cl.
CPC .............. *A23L 27/30* (2016.08); *A23L 2/60* (2013.01); *A23L 7/143* (2016.08); *A23L 27/88* (2016.08); *C07C 39/10* (2013.01); *C07C 43/23* (2013.01); *A23V 2002/00* (2013.01)

(58) Field of Classification Search
CPC . A23L 27/30; A23L 27/88; A23L 2/60; C07C 39/10; C07C 43/23
See application file for complete search history.

(56) References Cited

U.S. PATENT DOCUMENTS

| | | | |
|---|---|---|---|
| 3,184,887 A | 5/1965 | Winter | |
| 4,296,260 A | 10/1981 | Zielke et al. | |
| 4,830,862 A | 5/1989 | Braun et al. | |
| 4,925,686 A | 5/1990 | Kastin | |
| 7,052,725 B2 | 5/2006 | Chang et al. | |
| 8,877,922 B2 | 11/2014 | Tachdjian et al. | |
| 9,993,017 B2 | 6/2018 | Rhyu et al. | |
| 2002/0068123 A1 | 6/2002 | Verhagen et al. | |
| 2008/0107775 A1 | 5/2008 | Prakash et al. | |
| 2011/0160311 A1* | 6/2011 | Prakash | A23L 2/60 514/777 |
| 2014/0093630 A1 | 4/2014 | Shigemura et al. | |
| 2014/0094453 A1 | 4/2014 | Tachdjian et al. | |
| 2014/0271996 A1 | 9/2014 | Prakash et al. | |
| 2014/0272068 A1 | 9/2014 | Prakash et al. | |

FOREIGN PATENT DOCUMENTS

| | | |
|---|---|---|
| CN | 101557726 A | 10/2009 |
| GB | 1227744 A | 4/1971 |
| WO | WO-2013077668 A1 | 5/2013 |

OTHER PUBLICATIONS

Extended European Search Report dated Feb. 22, 2018, in European Patent Application 15839303.3, which corresponds to U.S. Appl. No. 15/509,817.
Goodwin, J. C., et al., "Structure-Taste Relationships among Cyclic Glycols, Levoglucosan, and Methyl Glycopyranosides," *J. Agric. Food Chem.*, vol. 29(5): 929-935 (1981).
PubChem Substance summary for CID 10383, 3,5-Dimethoxyphenol; Record created Mar. 26, 2005.
PubChem Substance summary for CID 71648, 5-Methoxyresorcinol; Record created Mar. 27, 2005.
PubChem Substance summary for CID 592988, 3,5-Dimethoxyphenol acetate; Record created Mar. 27, 2005.
PubChem Substance summary for CID 119929, 3,5-Dipropoxyphenol; Record created Jul. 19, 2005.
PubChem Substance summary for CID 75535, 1,3,5-Triethoxybenzene; Record created Aug. 8, 2005.
PubChem Substance summary for CID 119928, 5-Ethoxyresorcinol; Record created Aug. 8, 2005.
PubChem Substance summary for CID 10398184, 5-hydroxy-1,3-phenylene diacetate; Record created Oct. 25, 2006.
Shallenberger, R. S., "Sweetness Theory and its Application in the Food Industry," *Food Technology*, vol. 52(7): 72-76 (1998).
Hammond, C.T. and Mahlberg, P.G., "Phloroglucinol glucoside as a natural constituent of *Cannabis saliva*," *Phytochemistry* 37(3):755-756, Elsevier Science Ltd., Great Britain (1994).
International Preliminary Report on Patentability and Written Opinion for International Application No. PCT/US2015/049354, The International Bureau of WIPO, Geneva, Switzerland, dated Mar. 14, 2017, 7 pages.
International Search Report for International Application No. PCT/US2015/049354, ISA/US, Commissioner for Patents, Virginia, United States, dated Dec. 14, 2015, 3 pages.

* cited by examiner

*Primary Examiner* — Nikki H. Dees
(74) *Attorney, Agent, or Firm* — Sterne, Kessler, Goldstein & Fox

(57) ABSTRACT

The present disclosure provides sweetener compositions, methods of using these compositions, and foods, beverages, and syrups comprising these compositions. The sweetener composition can comprise a sweetener and a sweetness enhancer. The composition can further comprise at least one supplemental sweetness enhancer and/or a salt.

20 Claims, 4 Drawing Sheets

SWEETNESS ENHANCER

FIELD OF DISCLOSURE

The present disclosure is directed to enhancing the sweetness of sweeteners. The present disclosure is further directed to methods and compositions utilizing a sweetness enhancer to reduce the level of added sweeteners in beverage and food products.

BACKGROUND

Sweetness enhancers can be used to reduce the amount of added sugar in food products and beverages. Despite their utility, some sweetness enhancers have low water solubility making it difficult to solubilize them in beverages or in food products. Other known sweetness enhancers can leave an undesirable aftertaste or other undesired taste in a final product, have an insufficient shelf life, and/or be cost prohibitive for use on a commercial scale.

SUMMARY

The present disclosure provides methods and compositions for enhancing the sweetness of sweetener(s) using a compound of Formula I as a sweetness enhancer.

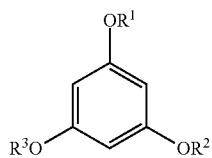

Formula I

In Formula I, each of $R^1$, $R^2$, and $R^3$ is independently selected from the group consisting of H, $C_1$-$C_3$ alkane, glucosyl, and —C(=O)$R^4$, and each $R^4$ is independently methyl or ethyl.

Compositions comprising the compound of Formula I and a sweetener are sweetener compositions.

The present disclosure further provides foods, beverages, syrups, and other formulations including the sweetener composition.

In certain embodiments, the sweetener composition can be in a dry form. However in other embodiments, the sweetener composition can be in liquid form.

In certain embodiments, the sweetener composition can further include a salt.

In certain embodiments, the sweetener composition can include one or more supplemental sweetness enhancers.

In some embodiments, the present disclosure provides a sweetener composition comprising at least one sweetener and a compound of Formula I:

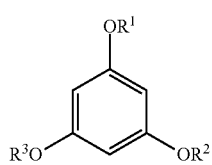

Formula I in an amount sufficient to enhance the sweetness of the at least one sweetener, wherein:

each of $R^1$, $R^2$, and $R^3$ is independently selected from the group consisting of H, $C_1$-$C_3$ alkane, glucosyl, and —C(=O)$R^4$; and wherein each $R^4$ is independently methyl or ethyl.

In certain embodiments, each of $R^1$, $R^2$, and $R^3$ is H.

In other embodiments, each of $R^1$, $R^2$, and $R^3$ is $CH_3$.

In other embodiments, at least one of $R^1$, $R^2$, or $R^3$ is glucosyl.

In certain embodiments, the sweetener composition further comprises at least one supplemental sweetness enhancer in an amount sufficient to further enhance the sweetness of the at least one sweetener but in an amount below the supplemental sweetness enhancer's sweetness recognition threshold concentration.

In certain embodiments, the supplemental sweetness enhancer is D-psicose, erythritol, rubusoside, rebaudioside B, rebaudioside C, trilobatin, phyllodulcin, brazzein, mogrosides, or a combination of any of the foregoing.

In certain embodiments, the sweetener is a nutritive sweetener.

In certain embodiments, the compound of Formula I and the nutritive sweetener are present in a weight ratio of from about 1:150 to about 1:50.

In certain embodiments, the sweetener is a non-nutritive sweetener.

In certain embodiments, the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

In certain embodiments, the compound of Formula I and non-nutritive sweetener are present in a weight ratio of from about 1.2:1 to about 1:1.2.

In certain embodiments, the sweetener composition is a tabletop sweetener.

In certain embodiments, the present disclosure provides an aqueous sweetener composition comprising water, an amount of at least one sweetener, and a compound of Formula I:

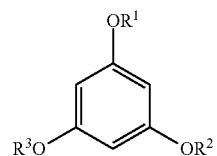

Formula I in an amount sufficient to enhance the sweetness of the at least one sweetener, wherein:

each of $R^1$, $R^2$, and $R^3$ is independently selected from the group consisting of H, $C_1$-$C_3$ alkane, glucosyl, and —C(=O)$R^4$; and wherein each $R^4$ is independently methyl or ethyl.

In certain embodiments, each of $R^1$, $R^2$, and $R^3$ is H.

In other embodiments, each of $R^1$, $R^2$, and $R^3$ is $CH_3$.

In still other embodiments, at least one of $R^1$, $R^2$, or $R^3$ is glucosyl.

In certain embodiments, the aqueous sweetener composition further comprises at least one supplemental sweetness enhancer in an amount sufficient to further enhance the sweetness of the at least one sweetener but in an amount below the supplemental sweetness enhancer's sweetness recognition threshold concentration.

In certain embodiments, the supplemental sweetness enhancer is D-Psicose, erythritol, rubusoside, rebaudioside B, rebaudioside C, trilobatin, phyllodulcin, brazzein, mogrosides, or a combination of any of the foregoing.

In certain embodiments, the concentration of the compound of Formula I in the aqueous sweetener composition is from about 40 to about 1000 ppm.

In other embodiments, the concentration of the compound of Formula I in the aqueous sweetener composition is from about 200 to about 800 ppm.

In still other embodiments, the concentration of the compound of Formula I in the aqueous sweetener composition is from about 400 to about 800 ppm.

In certain embodiments, the supplemental sweetness enhancer is selected from the group consisting of D-psicose, erythritol, and combinations thereof.

In certain embodiments, the sweetener in the aqueous sweetener composition is a nutritive sweetener.

In certain embodiments, the nutritive sweetener is selected from the group consisting of sucrose, fructose, glucose, and combinations thereof.

In certain embodiments, the nutritive sweetener is present at a concentration of from about 1% to about 20% by weight of the composition.

In certain embodiments, the concentration of the nutritive sweetener is from about 3% to about 16% by weight of the aqueous sweetener composition.

In certain embodiments, the aqueous sweetener composition has a pH of less than about 7.

In certain embodiments, the aqueous sweetener composition further comprises at least one salt.

In certain embodiments, the salt is sodium chloride.

In certain embodiments, the salt is present in the composition at a concentration of about 100 to about 800 ppm.

In certain embodiments, the aqueous sweetener composition is a beverage.

In certain embodiments, the amount of sweetener in the aqueous sweetener composition is at least about 25% less relative to a full calorie sweetener composition comprising the sweetener but lacking the compound of Formula I, wherein the aqueous sweetener composition has a sweetness equivalent to the full calorie sweetener composition lacking the compound of Formula I when sweetness is measured by a trained sensory discrimination panelist.

In certain embodiments, the present disclosure provides a syrup comprising an amount of at least one sweetener and a compound of Formula I:

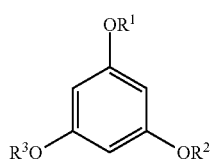

Formula I in an amount sufficient to enhance the sweetness of the at least one sweetener, wherein:
each of $R^1$, $R^2$, and $R^3$ is independently selected from the group consisting of H, $C_1$-$C_3$ alkane, glucosyl, and —C(=O)$R^4$; and
wherein each $R^4$ is independently methyl or ethyl.

In certain embodiments, each of $R^1$, $R^2$, and $R^3$ is H.

In other embodiments, each of $R^1$, $R^2$, and $R^3$ is $CH_3$.

In still further embodiments, at least one of $R^1$, $R^2$, or $R^3$ is glucosyl.

In certain embodiments, the syrup further comprises at least one supplemental sweetness enhancer in an amount sufficient to further enhance the sweetness of the at least one sweetener but in an amount below the supplemental sweetness enhancer's sweetness recognition threshold concentration.

In certain embodiments, the supplemental sweetness enhancer is selected from the group consisting of D-psicose, erythritol, and combinations thereof.

In certain embodiments, the compound of Formula I is present in the syrup at a concentration of about 240 to about 6000 ppm.

In other embodiments, the concentration of the compound of Formula I in the syrup is from about 1200 to about 4800 ppm.

In still other embodiments, the concentration of the compound of Formula I in the syrup is from about 2400 to about 4800 ppm.

In certain embodiments, the supplemental sweetness enhancer in the syrup is a rare sugar and the rare sugar is present at a concentration of at least about 1.2 weight percent to about 12 weight percent of the syrup.

In certain embodiments, the sweetener in the syrup is a nutritive sweetener.

In certain embodiments, the nutritive sweetener is selected from the group consisting of sucrose, fructose, glucose, and combinations thereof.

In certain embodiments, the nutritive sweetener is present in the syrup at a concentration of from about 6% to about 71% by weight of the syrup.

In other embodiments, the concentration of the nutritive sweetener in the syrup is from about 18% to about 52% by weight.

In certain embodiments, the syrup further comprises at least one salt.

In certain embodiments, the salt is sodium chloride.

The present disclosure further provides a food product comprising the sweetener composition described herein.

In certain embodiments, the food product is selected from the group consisting of cereal, snack bars, and dairy products.

In certain embodiments, the food product is selected from the group consisting of oatmeal, granola bars, and yogurt.

In certain embodiments, the present disclosure provides a sweetener composition comprising phloroglucinol, at least one nutritive or non-nutritive sweetener, and optionally a supplemental sweetness enhancer selected from the group consisting of D-psicose, erythritol, rubusoside, rebaudioside B, rebaudioside C, trilobatin, phyllodulcin, brazzein, mogrosides, and combination thereof.

In certain embodiments, the tabletop sweetener described herein further comprises at least one bulking agent.

The present disclosure further provides a packet comprising the tabletop sweetener described herein.

The present disclosure also provides a method of reducing the amount of sweetener in a food, beverage, or syrup, comprising replacing at least a portion of the sweetener in said food, beverage, or syrup, with a compound according to Formula I,

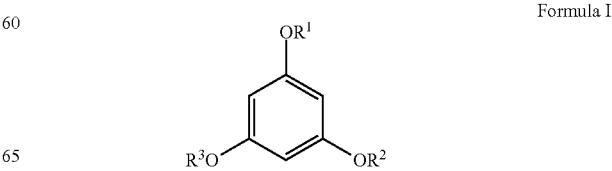

Formula I wherein:
each of $R^1$, $R^2$, and $R^3$ is independently selected from the group consisting of H, $C_1$-$C_3$ alkane, glucosyl, and —C(=O)$R^4$; and
wherein each $R^4$ is independently methyl or ethyl.

In certain embodiments, $R^1$, $R^2$, and $R^3$ are each H.

In other embodiments, $R^1$, $R^2$, and $R^3$ are each $CH_3$.

In still other embodiments, at least one of $R^1$, $R^2$, and $R^3$ is glucosyl.

In certain embodiments, the present disclosure provides a compound according to Formula I:

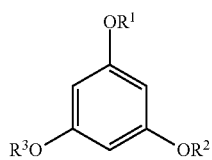

Formula I wherein each of $R^1$, $R^2$, and $R^3$ is independently selected from the group consisting of H, $C_1$-$C_3$ alkane, glucosyl, and —C(=O)$R^4$; and each $R^4$ is independently methyl or ethyl; provided that the compound of Formula I is not phloroglucinol, 1,3,5-trimethoxybenzene, phloroglucinol triacetate, or phloroglucinol glucoside.

BRIEF DESCRIPTION OF THE DRAWINGS

The foregoing summary, as well as the following detailed description of the embodiments, will be better understood when read in conjunction with the appended figures. For the purpose of illustration, the figures may describe the use of specific embodiments. It should be understood, however, that the formulations and compositions described herein are not limited to the precise embodiments discussed or described in the figures.

DETAILED DESCRIPTION

Figure 1:
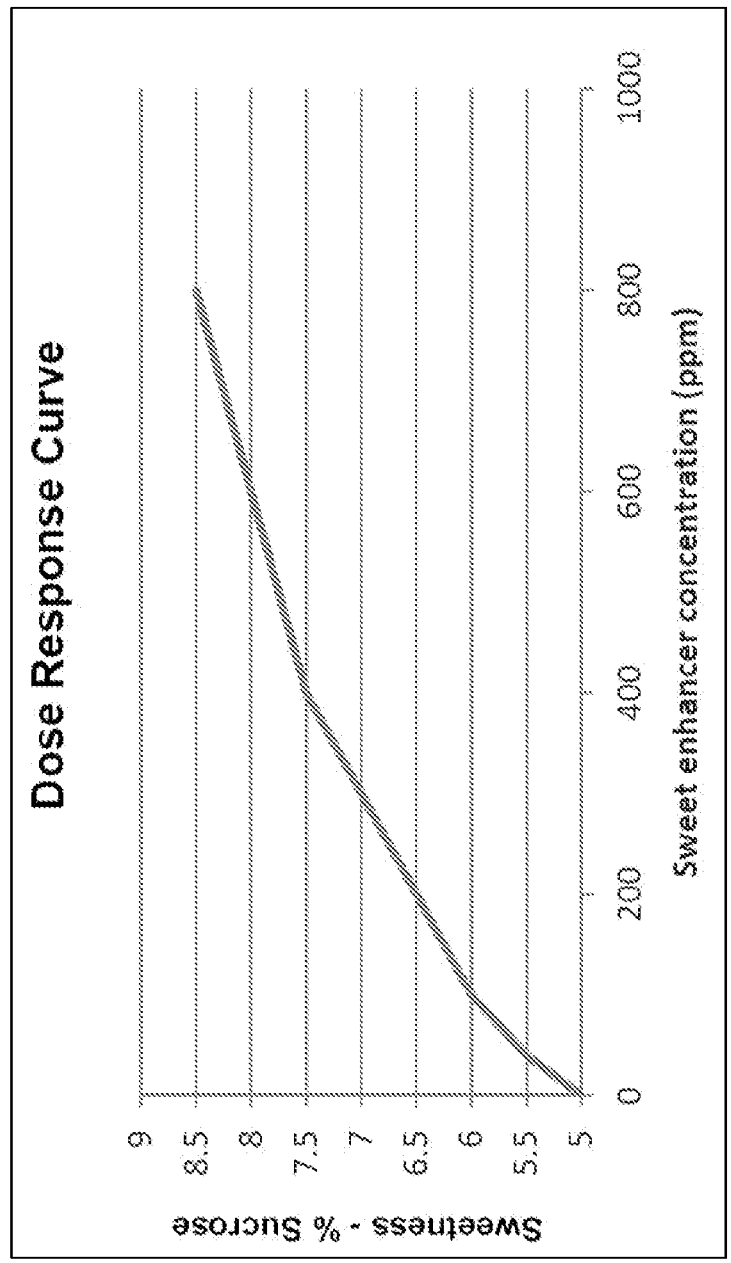
FIG. 1 is dose response curve showing how the sweetness of a 5% sucrose solution increases with increasing amounts of phloroglucinol.

Various examples and embodiments of the inventive subject matter disclosed here are possible and will be apparent to the person of ordinary skill in the art, given the benefit of this disclosure. In this disclosure reference to "some embodiments," "certain embodiments," "certain exemplary embodiments" and similar phrases each means that those embodiments are non-limiting examples of the inventive subject matter, and there are alternative embodiments which are not excluded.

Unless otherwise indicated or unless otherwise clear from the context in which it is described, alternative and optional elements or features in any of the disclosed embodiments and examples are interchangeable with each other. That is, an element described in one embodiment or example should be understood to be interchangeable or substitutable for one or more corresponding but different elements in another described example or embodiment and, likewise, an optional feature of one embodiment or example may optionally also be used in other embodiments and examples. More generally, the elements and features of any disclosed example or embodiment should be understood to be disclosed generally for use with other aspects and other examples and embodiments. A reference to a component or ingredient being operative or configured to perform one or more specified functions, tasks and/or operations or the like, is intended to mean that it can perform such function(s), task(s), and/or operation(s) in at least certain embodiments, and may well be able to perform also one or more other functions, tasks, and/or operations.

The articles "a," "an," and "the" are used herein to refer to one or to more than one (i.e., to at least one) of the grammatical object of the article. By way of example, "an element" means one element or more than one element.

The word "comprising" is used in a manner consistent with its open-ended meaning, that is, to mean that a given product or process can optionally also have additional features or elements beyond those expressly described.

As used herein, the term "about" means ±10% of the noted value. By way of example only, a composition comprising "about 30 weight percent" of a compound could include from 27 weight percent of the compound up to and including 33 weight percent of the compound.

The terms "beverage concentrate," "concentrate," and "syrup" are used interchangeably throughout this disclosure and refer to an aqueous sweetener composition suitable for use in beverage preparation. Exemplary embodiments are described elsewhere in this disclosure.

As used herein, the term "Brix" means the sugar content of an aqueous solution (w/w). By way of example only, a solution that is 1 degree Brix contains 1 g of sucrose in 100 grams of solution, while a solution that is 5 degrees Brix contains 5 g sucrose in 100 g solution.

As used herein, the phrase "edible consumables" means a food, beverage, or an ingredient of a food or beverage suitable for human or animal consumption.

The term "sweetness recognition threshold concentration," as generally used herein, is the lowest known concentration of a given sweetener or combination of sweeteners that is perceivable by the human sense of taste, typically around about 1.5% sucrose equivalence.

As used herein, "taste" refers to a combination of sweetness perception, temporal effects of sweetness perception, i.e., on-set and duration, off-tastes, e.g. bitterness and metallic taste, residual perception (aftertaste), and tactile perception, e.g. body and thickness.

As used herein, a "full-calorie" beverage formulation is one fully sweetened with a nutritive sweetener.

As used herein the term "glucosyl" refers to the radical having the formula:

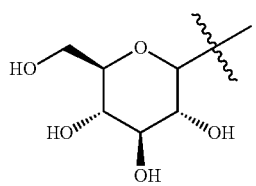 [SMILES: *C1O[C@H](CO)[C@@H](O)[C@H](O)[C@H]1O]

The term "nutritive sweetener" refers generally to sweeteners which provide significant caloric content in typical usage amounts, e.g., more than about 5 calories per 8 oz. serving of a beverage.

As used herein, the term "non-nutritive sweetener" refers to all sweeteners other than nutritive sweeteners.

As used herein, a "potent sweetener" means a sweetener which is at least twice as sweet as sugar, i.e. a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar. Potent sweeteners include both nutritive (e.g., Lo Han Guo juice concentrate) and non-nutritive sweeteners (e.g., typically, Lo Han Guo powder). In addition, potent sweeteners include both natural potent sweeteners (e.g., steviol glycosides, Lo Han Guo, etc.) and artificial potent sweeteners (e.g., neotame, etc.). However, for natural beverage products, only natural potent sweeteners are employed.

As used herein, the phrase "phloroglucinol glucoside" refers to the compound having the structure:

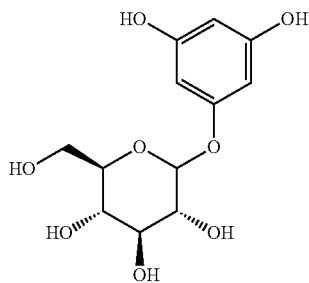 [SMILES: OC[C@H]1OC(Oc2cc(O)cc(O)c2)[C@H](O)[C@@H](O)[C@@H]1O]

As used herein, the phrase "weight percent" refers to a weight percent calculated based on the total weight of a given composition or formulation. By way of example only, a sweetener composition comprising 5 g of a sweetness enhancer as described herein and 95 g of a nutritive sweetener, would comprise 5 weight percent of the sweetness enhancer and 95 weight percent of the nutritive sweetener.

As used in this disclosure, unless otherwise specified, the term "added," "combined," and terms of similar character mean that the multiple ingredients or components referred to (e.g., one or more sweeteners, sweetness enhancers, etc.) are combined in any manner and in any order, with or without stirring.

The sweetness enhancers described in this disclosure are suitable for reducing the amounts of nutritive and/or non-nutritive sweeteners in foods and beverages while maintaining the desired sweet taste.

It has been surprisingly discovered that compounds of Formula I, below, unexpectedly act as sweetness enhancers.

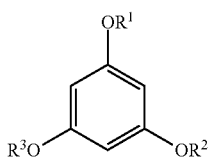

Formula I

In Formula I, each of $R^1$, $R^2$, and $R^3$ is independently selected from the group consisting of H, $C_1$-$C_3$ alkane, glucosyl, and —C(=O)$R^4$. Each $R^4$ is independently methyl or ethyl.

Compounds of Formula I enhance the sweetness of nutritive and non-nutritive sweeteners and allow manufacturers to reduce the amount of sweetener used in a given food or beverage.

In certain embodiments, one or more compounds of Formula 1 can be combined with one or more sweeteners to form a sweetener composition. In certain embodiments, this blend can be a granular or powdered composition suitable for use as a tabletop sweetener or for addition to food or beverage products. Alternatively, the sweetener composition can be an aqueous solution. The aqueous solution can be a liquid tabletop sweetener or a sweetener solution that is then added to other ingredients to form a beverage or beverage syrup (concentrate). In certain embodiments the aqueous solution can be a syrup. Alternatively, the compound of Formula I can be added directly to food or beverage products already containing a sweetener.

In certain embodiments, the sweetener composition can comprise from about 0.0005 weight percent to about 75 weight percent of one or more compounds of Formula 1. In other embodiments, the sweetener composition can comprise from about 0.0005 weight percent to about 65 weight percent; from about 0.0005 weight percent to about 55 weight percent; from about 0.0005 weight percent to about 45 weight percent; from about 0.0005 weight percent to about 35 weight percent; from about 0.0005 weight percent to about 25 weight percent; from about 0.0005 weight percent to about 20 weight percent; from about 0.0005 weight percent to about 25 weight percent; from about 0.0005 weight percent to about 15 weight percent; from about 0.001 to about 10 weight percent; from about 0.001 to about 5 weight percent, from about 0.001 to about 1 weight percent; or from about 0.001 weight percent to about 0.5 weight percent of the one or more compounds of Formula I.

In embodiments where the sweetener composition is an aqueous solution, such as a beverage suitable for use without further dilution, the weight percentage of the one or more compounds of Formula I in the composition can correspond to a concentration of less than about 1000 ppm, such as, for example, from about 5 ppm to about 800 ppm, from about 50 ppm to about 600 ppm, or from about 100 ppm to about 400 ppm.

Without wishing to be bound by any particular theory, it is believed that using a compound of Formula I as a sweetness enhancer in the compositions described herein allows for at least a 25% reduction, by weight, in the amount of sweetener(s) in a given composition required to achieve the same sweetness level in an otherwise identical composition not including the compound of Formula I.

In certain embodiments, each of $R^1$, $R^2$, and $R^3$ in Formula I is H. This compound is known commercially as "phloroglucinol" (aka benzene-1,3,5-triol or 1,3,5-trihydroxybenzene; CAS 108-73-6.)

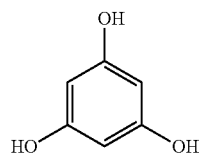

Phloroglucinol

Phloroglucinol is a phytochemical that exists in many plants. It can also be found in brown algae. Phloroglucinol has the molecular formula of $C_6H_6O_3$, a molecular weight of 126, a melting point of 217-219° C., a solubility of 1% in water, and acidity (pKa) of 8.45.

Phloroglucinol exists in two tautomeric forms: 1,3,5-trihydroxybenzene, which has phenol-like character, and 1,3,5-cyclohexanetrione, which has ketone-like character.

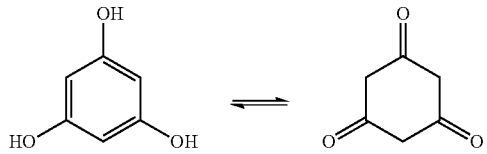 [SMILES: Oc1cc(O)cc(O)c1 ; O=C1CC(=O)CC(=O)C1]

Phloroglucinol is the backbone of many iso-flavonoids and can be prepared synthetically or be produced enzymatically, by fermentation, or by isolation from natural sources. It is also commercially available from many sources including, for example, Sigma-Aldrich. Although phloroglucinol is well known in the art, it has now been surprisingly discovered that it can act as a sweetness enhancer.

Because phloroglucinol is soluble in water, it does not require any additional ingredients or conditions to enhance its solubility—such as solubility enhancers or high mixing temperatures—when used in quantities sufficient to provide the desired amount of sweetness enhancement. Thus, in certain embodiments, appropriate amounts of phloroglucinol can be added to an aqueous solution at room temperature.

In addition to having suitable solubility for use in foods and beverages, phloroglucinol is stable and does not precipitate out of solution at the concentrations described herein, or break down at higher temperatures or when exposed to sunlight. As a result, use of phloroglucinol as a sweetness enhancer mitigates the need for special packaging or handling.

In certain embodiments, less than about 1000 ppm of phloroglucinol can be used to enhance the sweetness of a nutritive and/or non-nutritive sweetener. At this concentration, the quantity of sweetener used in a given food or beverage can be reduced by about 5 to about 40%, and in certain embodiments, from about 10 to about 25%, or about 25%, in comparison to the food or beverage not including phloroglucinol. At less than about 1000 ppm, phloroglucinol does not sweeten by itself, but is suitable to increase sweetness perception by, in certain embodiments, from about 0.5 to about 3 degrees Brix. Thus, in certain embodiments, the sweetener composition described herein can increase sweetness by about 0.5 Brix, about 1 Brix, about 1.5 Brix, about 2 Brix, about 2.5 Brix, or about 3 Brix.

In other embodiments, each of $R^1$, $R^2$, and $R^3$ in Formula I is $CH_3$. This compound is known commercially as 1,3,5-trimethoxybenzene (aka phloroglucinol trimethyl ether; CAS 621-23-8).

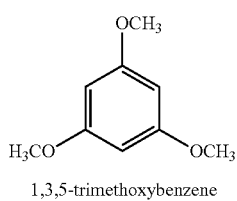 [SMILES: COc1cc(OC)cc(OC)c1]
1,3,5-trimethoxybenzene

Like phloroglucinol, 1,3,5-trimethoxybenzene is commercially available from manufacturers such as Sigma-Aldrich.

In other embodiments, each of $R^1$, $R^2$, and $R^3$ in Formula I is $-C(=O)R^4$ and each $R^4$ is $CH_3$. This compound is known commercially as phloroglucinol triacetate (CAS 2999-40-8) and is available from Matrix Scientific.

In still further embodiments, each of $R^1$, $R^2$, and $R^3$ in Formula I is $-C(=O)R^4$ and each $R^4$ is $CH_2H_3$.

In certain embodiments, the compound of Formula I is phloroglucinol glucoside (CAS 20217-60-9). Phloroglucinol glucoside was reported as a natural constituent of *Cannabis sativa* (C. Hammond, P. Mahlberg, Phytochemistry, 755 (1994)).

In other embodiments, at least two of $R^1$, $R^2$, and $R^3$ in Formula I is glucosyl.

Although in certain embodiments $R^1$, $R^2$, and $R^3$ are the same, embodiments wherein $R^1$ and $R^2$ are different and wherein $R^1$, $R^2$, and $R^3$ are all different are also contemplated and within the scope of this disclosure, whether or not expressly drawn.

By way of example, in certain embodiments, $R^1$ and $R^2$ can be H and $R^3$ can be methyl, ethyl, propyl, isopropyl, glucosyl, or $-C(=O)R^4$, with $R^4$ being methyl or ethyl. In particular embodiments, $R^3$ can be methyl. In other embodiments, $R^3$ can be glucosyl.

In other embodiments, $R^1$ and $R^2$ can be glucosyl and $R^3$ can be H or $CH_3$.

Sweeteners

As set forth in this disclosure, the sweetness enhancer of Formula I can be combined with one or more nutritive and/or non-nutritive sweeteners to form a sweetener composition. Sweeteners and combinations of sweeteners for use in the sweetener composition can be selected for any of their nutritional characteristics, taste profile, mouthfeel, or other organoleptic properties.

The sweeteners included in the formulations of the compositions and products disclosed here are edible consumables. The sweetener can be a nutritive or non-nutritive, natural or synthetic sweetener, or a combination of such sweeteners, so long as the sweetener or combination of sweeteners provides a taste which is perceived as sweet by the sense of taste. The perception of flavoring agents and sweetening agents can depend to some extent on the interrelation of elements. Flavor and sweetness can also be perceived separately, i.e., flavor and sweetness perception can be both dependent upon each other and independent of each other. For example, when a large amount of a flavoring agent is used, a small amount of a sweetening agent can be readily perceptible and vice versa. Thus, the oral and olfactory interaction between a flavoring agent and a sweetening agent can involve the interrelationship of elements.

When used to sweeten, the sweetener or combination of sweeteners in the sweetener composition is present in an amount above the sweeteners' sweetness recognition threshold concentration.

Exemplary natural nutritive sweeteners suitable for use in the sweetener composition include crystalline or liquid sucrose, fructose, glucose, dextrose, maltose, trehalose, fructo-oligosaccharides, glucose-fructose syrup from natural sources such as apple, chicory, and honey; high fructose corn syrup, invert sugar, maple syrup, maple sugar, honey, brown sugar molasses, cane molasses, such as first molasses, second molasses, blackstrap molasses, and sugar beet molasses; sorghum syrup, and mixtures thereof.

Other sweeteners suitable for use in the sweetener composition include, but are not limited to, sugar alcohols such as erythritol, sorbitol, mannitol, xylitol, lactitol, isomalt, malitol, tagatose, trehalose, galactose, rhamnose, cyclodextrin, ribulose, threose, arabinose, xylose, lyxose, allose, altrose, mannose, idose, lactose, maltose, isotrehalose, neotrehalose, palatinose or isomaltulose, erythrose, deoxyribose, gulose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, and mixtures thereof.

Other sweeteners suitable for use in the sweetener composition include rare sugars such as D-allose, D-psicose (also known as D-allulose), L-ribose, D-tagatose, L-glucose, L-fucose, L-arabinose, D-turanose, D-leucrose, and mixtures thereof.

Exemplary artificial sweeteners suitable for use in the sweetener composition include, but are not limited to, saccharin, cyclamate, aspartame, neotame, advantame, acesulfame potassium, sucralose, mixtures thereof.

Exemplary natural non-nutritive potent sweeteners suitable for use in the sweetener composition disclosed here include steviol glycosides (e.g., stevioside, steviolbioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside 0, rebaudioside M, dulcoside A, rubusoside, iso-steviol glycosides such as iso-rebaudioside A, and mixtures thereof), Lo Han Guo powder, neohesperidin dihydrochalcone, trilobatin, glycyrrhizin, phyllodulcin, hernandulcin, osladin, polypodoside A, baiyunoside, pterocaryoside, thaumatin, monellin, monatin, mabinlins I and II, and mixtures thereof.

In other embodiments, Lo Han Guo juice concentrate can be used as a nutritive sweetener in the sweetener composition. Other natural non-nutritive potent sweeteners include, and mixture of any of them.

In certain embodiments, combinations of one or more natural nutritive sweeteners, one or more artificial sweeteners, and/or one or more natural non-nutritive potent sweeteners can be used. The foregoing notwithstanding, it should also be recognized that any of the identified sweeteners can, either in addition or instead of, act as supplemental sweetness enhancers, masking agents, or the like, when used in amounts below its (or their) sweetness perception threshold.

Supplemental Sweetness Enhancers

Although one or more compounds of Formula I can be used as a sweetness enhancer in the complete or substantial absence of further sweetness enhancers, in certain embodiments, the sweetener composition can include one or more compounds of Formula I and one or more supplemental sweetness enhancers. Without wishing to be bound by any particular theory, it is believed that addition of a supplemental sweetness enhancer allows for a reduction in the quantity of a compound of Formula I needed in a given composition.

Exemplary supplemental sweetness enhancers include, but are not limited to, D-psicose, erythritol, iso-rebaudioside A, rebaudioside B, rebaudioside C, rubusoside, trilobatin, phyllodulcin, brazzein, and/or mogrosides.

Additional supplemental sweetness enhancers are described in U.S. Patent Application Publication Nos. 2014/0271996 and 2014/0272068, along with U.S. Pat. No. 8,877,922, all of which are incorporated by reference in their entireties.

In certain embodiments, the one or more supplemental sweetness enhancers enhance the sweetness of whatever sweeteners are present in the sweetener composition, but are present in an amount below the supplemental sweetness enhancer's sweetness recognition threshold concentration.

In certain embodiments, the sweetener composition can comprise phloroglucinol and one or more supplemental sweetness enhancers. In other embodiments, the sweetener composition can comprise phloroglucinol trimethyl ether and one or more supplemental sweetness enhancers.

Salts as Supplemental Sweetness Enhancers

Surprisingly, it has been found that addition of one or more salts, and in particular, sodium chloride, can act as a supplemental sweetness enhancer when used in combination with a compound of Formula I. Thus, in certain embodiments, in addition to the one or more compounds of Formula I and the sweetener or mixture of sweeteners, the sweetener composition can further include at least one salt. Use of a salt allows for the reduction in the quantity of the compound of Formula I that needs to be included in the composition, while at the same time enhancing the overall sweetness of composition in which it is included.

Suitable salts that can be included in the composition include sodium chloride or commercial salts obtained from various sources such as sea salt. The salt can be added in an amount sufficient to enhance the effectiveness of a compound of Formula I, such as phloroglucinol. These salts, and in particular embodiments, sodium chloride, can be present in amounts ranging from about 200 to about 400 ppm or at about 10 weight %, about 20 weight %, about 30 weight %, about 40 weight %, or at about 50 weight % relative to the quantity of the compound of Formula I in a given formulation. In certain embodiments, salt allows the quantity or concentration of the compound of Formula I to be reduced by about 10%, about 15%, about 20%, about 25%, about 30%, about 35%, about 40%, about 45%, about 50%, or about 55% without affecting the overall sweetness of the composition.

Rare Sugar Supplemental Sweetness Enhancers

In certain embodiments, the present disclosure provides sweetener composition or a food or beverage composition comprising a combination of a compound of Formula I, such as phloroglucinol, phloroglucinol trimethyl ether, or phloroglucinol glucoside, a rare sugar as a supplemental sweetness enhancer, and one or more nutritive or non-nutritive sweeteners. Exemplary rare sugars include D-psicose (also referred to as D-allulose), D-allose, L-ribose, D-tagatose, L-glucose, L-fucose, L-arabinose, D-turanose, D-leucrose, and mixtures thereof.

In one embodiment, a sugar-reduced beverage can be prepared using reduced quantities of sucrose or HFCS (High Fructose Corn Syrup), a compound of Formula I, and a rare sugar such as D-psicose. In certain embodiments, the compound of Formula I can be phloroglucinol. In other embodiments, the compound of Formula I can be phloroglucinol trimethyl ether. In another embodiment, the compound of Formula I can be phloroglucinol glucoside. Use of the compound of Formula I and D-psicose as the supplemental sweetness enhancer enables a desirable degree of sugar reduction while simultaneously permitting a reduction in the concentration of the compound of Formula I. The presence of a rare sugar can also help overall mouthfeel which can be decreased due to sugar reduction. In certain embodiments, the weight ratio of the compound of Formula I to D-psicose can be from about 1 to about 30.

In another embodiment, the present disclosure provides a non-caloric or low caloric beverage comprising one or more non-nutritive sweeteners, a compound of Formula I, and D-psicose as the supplemental sweetness enhancer. In certain embodiments, the compound of Formula I is phloroglucinol. In other embodiments, the compound of Formula I is phloroglucinol trimethyl ether. In another embodiment, the compound of Formula I is phloroglucinol glucoside. In embodiments comprising phloroglucinol, and without wishing to be bound by any particular theory, it is believed that the phloroglucinol can enhance the sweetness of non-nutritive sweeteners, in particular natural non-nutritive sweeteners such as rebaudioside A, without affecting the off-taste or after taste of the rebaudioside A. Similarly, and without wishing to be bound by any particular theory, it is believed that a blend of phloroglucinol and D-psicose allows for a) a reduction in the concentration of both rebaudioside A and phloroglucinol without sacrificing the overall sweetness of the beverage; and b) improves mouthfeel and decreases off-taste and after-taste.

In other embodiments, a compound of Formula I such as phloroglucinol, phloroglucinol trimethyl ether, or phloroglucinol glucoside, and a rare sugar can be combined with other steviol glycosides or natural high potency sweeteners. Suitable steviol glycosides and natural high potency sweeteners include, but are not limited to, rebaudioside C, rebaudioside D, rebaudioside E, rebaudioside M, monatin and its salts, mogroside IV, mogroside V, brazzein, thaumatin, and mixtures of any of the foregoing.

In other embodiments, a compound of Formula I, such as phloroglucinol, phloroglucinol trimethyl ether, or phloroglucinol glucoside, can be used in combination with D-psicose and/or erythritol in further combination with one or more artificial non-nutritive sweeteners discussed above, such as aspartame.

Sugar Alcohol Supplemental Sweetness Enhancers

In certain embodiments, the present disclosure provides sweetener compositions and food and beverage formulations comprising a compound of Formula I, a sugar alcohol as the supplemental sweetness enhancer, and one or more sweeteners. Suitable sugar alcohols include erythritol, sorbitol, mannitol, xylitol, lactitol, isomalt, malitol, and mixture thereof.

In certain embodiments, the compound of Formula I can be phloroglucinol. In other embodiments, the compound of Formula I can be phloroglucinol trimethyl ether. In another embodiment, the compound of Formula I can be phloroglucinol glucoside.

Non-Nutritive Natural Supplemental Sweetness Enhancers

In certain embodiments, this disclosure provides a sweetener composition as well as food and beverage formulations comprising one or more compounds of Formula I, such as phloroglucinol or phloroglucinol or phloroglucinol trimethyl ether, one or more non-nutritive natural enhancers as the supplemental sweetness enhancer, and one or more sweeteners. In certain embodiments, the compound of Formula I can be phloroglucinol. In other embodiments, the compound of Formula I can be phloroglucinol trimethyl ether.

Suitable non-nutritive natural enhancers include steviol glycosides. Suitable steviol glycosides, include, but are not limited to, stevioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside O, rebaudioside M, rubusoside, dulcoside A, iso-steviol glycosides such as iso-rebaudioside A, and mixtures thereof. In a particular embodiment, the supplemental sweetness enhancer can be rubusoside, rebaudioside C or rebaudioside B.

In other embodiments, the non-nutritive natural enhancer supplemental sweetness enhancer can be a mogrol glycoside. Suitable mogrol glycosides, include, but are not limited to, mogroside V, isomogroside, mogroside IV, siamenoside, and mixtures thereof.

Benzoic Acid Derived Supplemental Sweetness Enhancers

In certain embodiments, this disclosure provides a sweetener composition as well as food and beverage formulations comprising one or more compounds of Formula I, such as phloroglucinol or phloroglucinol or phloroglucinol trimethyl ether, benzoic acid or a benzoic acid derivative as the supplemental sweetness enhancer, and one or more sweeteners. Suitable benzoic acid derivatives include, but are not limited to, hydroxybenzoic acids such as 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid and combinations thereof.

In certain embodiments, the compound of Formula I can be phloroglucinol. In other embodiments, the compound of Formula I can be phloroglucinol trimethyl ether. In other embodiments, the compound of Formula I can be phloroglucinol glucoside.

FEMA GRAS Supplemental Sweetness Enhancers

In certain embodiments, this disclosure provides a sweetener composition as well as food and beverage formulations comprising one or more compounds of Formula I, such as phloroglucinol or phloroglucinol or phloroglucinol trimethyl ether, a FEMA GRAS enhancer or flavor, and one or more sweeteners. Suitable FEMA GRAS enhancers include, but are not limited to, FEMA GRAS enhancer 4802, FEMA GRAS enhancer 4469, FEMA GRAS flavor 4701, FEMA GRAS enhancer 4720 (rebaudioside C), FEMA GRAS flavor 4774, FEMA GRAS enhancer 4708, FEMA GRAS enhancer 4728, FEMA GRAS enhancer 4601 (rebaudioside A) and combinations thereof. In a particular embodiment, the sweetness enhancer is FEMA GRAS flavor 4701. In another particular embodiment, the sweetness enhancer is FEMA GRAS flavor 4774.

In certain embodiments, the compound of Formula I can be phloroglucinol. In other embodiments, the compound of Formula I can be phloroglucinol trimethyl ether. In another embodiment, the compound of Formula I can be phloroglucinol glucoside Other Supplemental Sweetness Enhancers In certain embodiments, this disclosure provides a sweetener composition and a food or beverage formulation comprising one or more compounds of Formula I, such as phloroglucinol or phloroglucinol or phloroglucinol trimethyl ether, one or more sweeteners, and a compound selected from the group consisting of: phyllodulcin, brazzein, a dihydrochalcone, 4-amino-5-(cyclohexyloxy)-2-methylquinoline-3-carboxylic acid or a salt thereof, 4-amino-5,6-dimethylthieno[2,3-d]pyrimidine-2(1H)-one or an analog as disclosed in US 2014/0093630, the contents of which are incorporated by reference in their entirety, and a compound according to Formula II, below, as disclosed in U.S. Pat. No. 8,877,922 and U.S. Patent Application Publication No. 2014/0094453, the contents of which are both incorporated by reference in their entirety

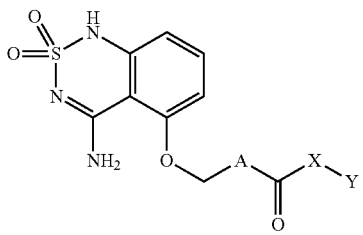

wherein A is an optionally substituted four to eight-membered azacyclic ring; X is a covalent bond or —NR$^1$—; R$^1$ is hydrogen or C$_1$ to C$_6$ alkyl; and Y is alkyl, substituted alkyl, heteroalkyl, substituted heteroalkyl, carbocyclyl, substituted carbocyclyl, heterocyclyl, substituted heterocyclyl, aryl, substituted aryl, heteroaryl, substituted heteroaryl, aralkyl, substituted aralkyl, heteroarylalkyl, or substituted heteroarylalkyl. A particular example is FEMA #4802.

Exemplary dihydrochalcones include, but are not limited to, trilobatin.

In certain embodiments, the compound of Formula I is phloroglucinol, phloroglucinol trimethyl ether, or phloroglucinol glucoside.

Dry Blends/Tabletop Compositions

In certain embodiments, the sweetener composition can be a dry blend of a compound of Formula I and a nutritive sweetener. For example, the ratio of the compound of Formula I to nutritive sweetener in the dry blend can be from about 1:400 to about 1:20 by weight, and in certain embodiments, from about 1:250 to about 1:50 by weight. In certain embodiments, the compound of Formula I is phloroglucinol. In other embodiments, the compound of Formula I is phloroglucinol trimethyl ether. In other embodiments, the compound of Formula I is phloroglucinol glucoside.

In certain embodiments, the sweetener composition can also be a dry blend of a compound of Formula I and non-nutritive sweetener. In certain embodiments, the ratio of phloroglucinol to non-nutritive sweetener in the dry blend can be from about 3:1 to about 1:3 by weight, and in certain embodiments, from about 1.2:1 to about 1:1.2 by weight. In certain embodiments, the compound of Formula I is phloroglucinol. In other embodiments, the compound of Formula I is phloroglucinol trimethyl ether. In another embodiment, the compound of Formula I is phloroglucinol glucoside.

In certain embodiments, the dry blend can also contain one or more salts in an amount effective to enhance the sweetening effect of the compound of Formula I. In certain embodiments, the salt is sodium chloride and the ratio of sodium chloride to the compound of Formula I can be from about 2.5:1 to about 1:2.5 by weight. In other embodiments, the ratio of sodium chloride to the compound of Formula I can be from about 1:1 to about 1:2 by weight. In certain embodiments, the compound of Formula I is phloroglucinol. In other embodiments, the compound of Formula I is phloroglucinol trimethyl ether. In another embodiment, the compound of Formula I is phloroglucinol glucoside.

The dry blend sweetener composition can also contain one or more supplemental sweetness enhancers as discussed above. Addition of a supplemental sweetness enhancer allows for a reduction in the amount of the compound of Formula I in the composition.

The dry blend sweetener composition can be a granular or powdered composition such as for use as a tabletop sweetener. Alternatively, the dry blend can be added to food products for baking or as a topping or to a liquid, such as to form a beverage from a powder e.g. chocolate milk, or Instant QUAKER Oats.

The dry blend sweetener composition can further include a binding or bulking agent, an anti-caking agents, and/or a flavor. Suitable binding or bulking agents include, but are not limited to maltodextrin; dextrose-maltodextrin blends, hydroxypropylmethyl cellulose, carboxymethyl cellulose, polyvinylpyrrolidone, and mixtures thereof. Suitable anti-caking agents include, but are not limited to alumino silicate, magnesium carbonate, and combinations thereof.

Aqueous Compositions

In other embodiments, the sweetener composition can be included in an aqueous formulation, the formulation comprising water, a sweetener, and a compound of Formula I. In certain embodiments, the compound of Formula I can be phloroglucinol. In other embodiments, the compound of Formula I can be phloroglucinol trimethyl ether. In certain embodiments, the sweetener is a nutritive sweetener, a non-nutritive sweetener, or a combination thereof.

In certain embodiments, the aqueous formulation can further include at least one supplemental sweetness enhancer, a salt, or a combination thereof.

Beverage Compositions

In certain embodiments, the aqueous composition can be a beverage. Any effective amount of a compound of Formula I can be added to the beverage compositions in order to enhance sweetness. That said, in certain embodiments, the concentration of the compound of Formula I in a beverage composition can range from about 40 to about 1000 ppm. In other embodiments, the concentration of the compound of Formula I can be at least about 100 ppm, at least about 200 ppm, at least about 300 ppm, at least about 400 ppm, at least about 500 ppm, at least about 600 ppm, at least about 700 ppm, at least about 800 ppm, at least about 900 ppm, or at least about 1000 ppm. In particular embodiments, the concentration of the compound of Formula I in the beverage composition can range from about 200 ppm to about 800 ppm and in still further embodiments, from about 400 ppm to about 500 ppm.

In certain embodiments, one or more nutritive sweeteners can be present in a beverage compositions in an amount of from about 1% to about 20% by weight of the beverage composition, such as from about 3% to about 16% by weight, or from about 5% to about 12% by weight, depending upon the desired level of sweetness in the beverage composition.

In certain embodiments, non-nutritive sweeteners can be present in the beverage composition in an amount ranging from about 1 to about 600 ppm, depending upon the particular non-nutritive sweetener(s) being used and the desired level of sweetness in the beverage composition.

In certain embodiments, one or more salts can be included in the beverage composition in any effective amount. In other embodiments, salt concentration can range from about 100 ppm to about 1000 ppm, or in a further embodiment from about 200 ppm to about 800 ppm. In particular embodiments, the salt can be sodium chloride. In certain embodiments, the beverage composition can be completely or substantially salt free.

The beverage composition can further comprise one or more supplemental sweetness enhancers. In certain embodiments, the supplemental sweetness enhancer can be present at a concentration below its sweetness recognition threshold concentration.

For example, and in certain embodiments, the beverage composition can contain up to about 2 weight percent each of D-psicose, erythritol, or combination thereof. In some embodiments, D-psicose and/or erythritol can be present in an amount ranging from about 0.5 to about 2.0 weight percent. Alternatively, D-psicose can be present in an amount ranging from about 0.5 to about 2.0 weight percent and erythritol can be present in an amount ranging from about 0.5 to about 1 weight percent.

In certain embodiments, the beverage composition can further comprise other ingredients such as antioxidants, food grade acids, and food grade bases. If the beverage composition is intended for use as a beverage product, other beverage components such as flavorants, colors, preservatives, carbon dioxide, buffering salts, and the like, can also be present. If the beverage composition is intended for use in food products, other food components can also be present.

In certain embodiments, the beverage composition is a beverage, i.e. a ready to drink liquid formulation. Beverages include, but are not limited to, carbonated and non-carbonated soft drinks, fountain beverages, frozen ready-to-drink beverages, coffee, tea, and other brewed beverages, dairy beverages, flavored waters, enhanced waters, juices such as fruit juice (including diluted and ready to drink concentrated juices), fruit juice-flavored drinks, sport drinks, smoothies, functionally enhanced beverages such as caffeinated energy drinks, and alcoholic products. In particular embodiments, the beverage composition can be a cola beverage.

It should be understood that beverages and other beverage products in accordance with this disclosure can have any of numerous different specific formulations or constitutions. The formulation of a beverage product in accordance with this disclosure can vary, depending upon such factors as the product's intended market segment, its desired nutritional characteristics, flavor profile, and the like. For example, further ingredients can be added to the formulation of a particular beverage embodiment. Further ingredients include, but are not limited to, one or more additional sweeteners in addition to any sweetener already present, flavorings, electrolytes, vitamins, fruit juices or other fruit products, tastants, masking agents, flavor enhancers, carbonation, or any combination of the foregoing. These can be added to any of the beverage compositions to vary the taste, mouthfeel, and/or nutritional characteristics of the beverage composition.

In certain embodiments, a beverage composition in accordance with this disclosure can comprise water, a sweetener, a compound of Formula I, an acidulant, and a flavoring. Exemplary flavorings include, but are not limited to, cola flavoring, citrus flavoring, spice flavorings, and combinations thereof. Carbonation in the form of carbon dioxide can be added for effervescence. In certain embodiments, preservatives can be added if desired or necessary, depending upon factors including the presence of other ingredients, production technique, desired shelf life, etc. In certain embodiments, caffeine can be added to the beverage. In particular embodiments, the compound of Formula I is phloroglucinol. In other embodiments, the compound of Formula I is phloroglucinol trimethyl ether. In another embodiment, the compound of Formula I is phloroglucinol glucoside.

Certain exemplary embodiments of the beverages disclosed here are cola-flavored carbonated beverages, characteristically containing, in addition to the ingredients included in the beverage compositions disclosed herein, carbonated water, sweetener, kola nut extract and/or other flavorings, caramel coloring, phosphoric acid, and optionally other ingredients. Additional and alternative suitable ingredients will be recognized by those skilled in the art given the benefit of this disclosure.

Concentrated Aqueous Compositions

Beverages are typically not prepared in large batches. Instead, a syrup (alternatively referred to as a beverage concentrate or concentrate), water, and optionally carbon dioxide are combined at the time of use or at the time of bottling or dispensing a beverage. The syrup is a concentrated solution of many of the soluble ingredients typically included in a given beverage.

Thus, in certain embodiments, the aqueous composition can be a beverage concentrate. At least certain exemplary embodiments of the beverage concentrates contemplated can be prepared with an initial volume of water to which at least a sweetener and at least a compound of Formula I are added. In certain embodiments, full strength beverage compositions can be formed from the beverage concentrate by adding further volumes of water to the concentrate. In certain embodiments, a full strength beverage can be prepared from a concentrate by combining approximately 1 part concentrate with about 3 to about 7 parts water. In certain embodiments, the full strength beverage can be prepared by combining 1 part concentrate with 5 parts water. In certain exemplary embodiments the water added to the concentrate to form the full strength beverages can be carbonated.

In certain embodiments, the concentration of a compound of Formula I in the beverage concentrate can range from about 240 to about 6000 ppm. In certain embodiments, the concentration of the compound of Formula I can beat least about 1200 ppm, at least about 1800 ppm, at least about 2400 ppm, or about 6000 ppm. In still further embodiments, the concentration of the compound of Formula I can range from about 1200 to about 1800 ppm or from about 2400 ppm to about 4800 ppm.

In certain embodiments, nutritive sweeteners can be present in the concentrate at from about 6% to about 71% by weight of the beverage concentrate, such as from about 18% to about 62% by weight, or from about 30% to about 45% by weight, depending upon the desired level of sweetness for the final aqueous composition (e.g. beverage.)

In certain embodiments, non-nutritive sweeteners can be present at from about 6 to about 3600 ppm depending upon the particular non-nutritive sweetener being used and the desired level of sweetness for the final aqueous composition comprising the concentrate.

In certain embodiments, one or more salts can be included in the syrup. Any effective amount of salt can be added, but in certain embodiments the salt concentration in the syrup ranges from about 600 ppm to about 6000 ppm, and in certain embodiments, from about 1200 ppm to about 2400 ppm. In certain embodiments, the syrup can be completely or substantially salt free.

In certain embodiments, the syrups can further comprise a supplemental sweetness enhancers in an amount such that the concentration of the supplemental sweetness enhancer will be below its sweetness recognition threshold concentration in a final product.

For example, in certain embodiments, the syrup can contain up to about 18 weight percent of D-psicose, erythritol, or combination thereof. In other embodiments, D-psicose or erythritol can be present in an amount of from about 3 to about 9 weight percent. Alternatively, D-psicose can be present in an amount ranging from about 3 to about 9 weight percent and erythritol can be present in an amount of from about 3 to about 6 weight percent.

Water

Water is a basic ingredient in the aqueous compositions described herein, typically being the vehicle or primary liquid portion in which the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free from objectionable minerals, tastes and odors, free from organic matter, low in alkalinity and of acceptable microbiological quality based on industry and government standards applicable at the time of producing the beverage.

In certain embodiments, water can be present at a level of from about 20 weight percent to about 99.9 weight percent in the aqueous compositions disclosed herein. In certain beverage embodiments, the quantity of water can range from about 80 weight percent to about 99.9 weight percent of the beverage. In at least certain exemplary embodiments the water used in beverages and concentrates disclosed here is "treated water," which refers to water that has been treated to reduce the total dissolved solids of the water prior to optional supplementation with calcium as disclosed in U.S. Pat. No. 7,052,725, which is incorporated by reference in its entirety.

Methods of producing treated water are known to those of ordinary skill in the art and include deionization, distillation, filtration and reverse osmosis ("r-o"), among others. The terms "treated water," "purified water,", "demineralized water," "distilled water," and "r-o water" are understood to be generally synonymous in this discussion, referring to water from which substantially all mineral content has been removed, typically containing no more than about 500 ppm total dissolved solids, e.g. 250 ppm total dissolved solids.

Uses

The sweetener composition, whether a dry blend or in liquid form, can be utilized in any food or beverage product typically including a sweetener, including, but not limited to, those uses already discussed throughout this disclosure. In addition to those uses already specified, the sweetener composition described herein is also suitable for use in cooking, baking (i.e. for use in cookies, cakes, pies, brownies, breads, granola bars, etc.), for preparing sweetened toppings, such as icings, and for use in jellies, jams, preserves, Instant QUAKER Oats, and the like. It is similarly suitable for use in frozen dairy products, such as ice cream, as well as in whipped toppings. Although in certain embodiments, the sweetener composition can be dissolved in the food or beverage, in other embodiments, the sweetener composition can be present in the food or beverage as part of a suspension or emulsion.

Natural Embodiments

Certain embodiments of the described compositions can be "natural" in that they do not contain anything artificial or synthetic (including any color additives regardless of source) that would not normally be expected to be in the food. As used herein, therefore, a "natural" composition is defined in accordance with the following guidelines: Raw materials for a natural ingredient exists or originates in nature. Biological synthesis involving fermentation and enzymes can be employed, but synthesis with chemical reagents is not utilized. Artificial colors, preservatives, and flavors are not considered natural ingredients. Ingredients may be processed or purified through certain specified techniques including at least: physical processes, fermentation, and enzymolysis. Appropriate processes and purification techniques include at least: absorption, adsorption, agglomeration, centrifugation, chopping, cooking (baking, frying, boiling, roasting), cooling, cutting, chromatography, coating, crystallization, digestion, drying (spray, freeze drying, vacuum), evaporation, distillation, electrophoresis, emulsification, encapsulation, extraction, extrusion, filtration, fermentation, grinding, infusion, maceration, microbiological (rennet, enzymes), mixing, peeling, percolation, refrigeration/freezing, squeezing, steeping, washing, heating, mixing, ion exchange, lyophilization, osmose, precipitation, salting out, sublimation, ultrasonic treatment, concentration, flocculation, homogenization, reconstitution, enzymolysis (using enzymes found in nature). Processing aids (currently defined as substances used as manufacturing aids to enhance the appeal or utility of a food component, including clarifying agents, catalysts, flocculants, filter aids, and crystallization inhibitors, etc. See 21 CFR § 170.3(o)(24)) are considered incidental additives and may be used if removed appropriately.

Additional Ingredients

In certain embodiments, the compositions disclosed herein can contain a flavor composition, for example, natural, nature identical, and/or synthetic fruit flavors, botanical flavors, other flavors, and mixtures thereof. As used here, the term "fruit flavor" refers generally to those flavors derived from the edible reproductive part of a seed plant including those plants wherein a sweet pulp is associated with the seed, e.g., tomato, cranberry, and the like, and those having a small, fleshy berry. The term berry includes true berries as well as aggregate fruits, i.e., not "true" berries, but fruit commonly accepted as such. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime grapefruit, tangerine, mandarin orange, tangelo, and pomelo, apple, grape, cherry, and pineapple flavors. In certain embodiments concentrates and beverages comprise a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots, and leaves. Also included within the term "botanical flavor" are synthetically prepared flavors made to simulate botanical flavors derived from natural sources. Examples of such flavors include cola flavors, tea flavors, and mixtures thereof. The flavor component may further comprise a blend of several of the above-mentioned flavors. In certain exemplary embodiments of the beverage concentrates and beverages a cola flavor component is used or a tea flavor component. The particular amount of the flavor component useful for imparting flavor characteristics to the beverages of the present disclosure will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in at least certain exemplary embodiments of the beverage products disclosed here include, e.g., fruit, vegetable and berry juices. Juices may be employed in the present compositions in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices can be combined, optionally along with other flavorings, to generate a concentrate, beverage, or solid food having a desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, mandarin, melon, watermelon, and grapefruit. Numerous additional and alternative juices suitable for use in at least certain exemplary embodiments will be apparent to those skilled in the art given the benefit of this disclosure. In the compositions of the present disclosure employing juice, juice can be used, for example, at a level of at least about 0.2 weight percent of the composition. In certain embodiments juice can be employed at a level of from about 0.2 weight percent to about 40 weight percent. In further embodiments, juice can be used, if at all, in an amounts ranging from about 1 to about 20 weight percent.

Juices that are lighter in color can be included in the formulation of certain exemplary embodiments to adjust the flavor and/or increase the juice content of the beverage without darkening the beverage color. Examples of such juices include apple, pear, pineapple, peach, lemon, lime, orange, apricot, grapefruit, tangerine, rhubarb, cassis, quince, passion fruit, papaya, mango, guava, litchi, kiwi, mandarin, coconut, and banana. Deflavored and decolored juices can be employed if desired.

Other flavorings suitable for use in at least certain exemplary embodiments of the food and beverage products disclosed here include, e.g., spice flavorings, such as cassia, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings may be in the form of an extract, oleoresin, juice concentrate, bottler's base, or other forms known in the art. In at least certain exemplary embodiments, such spice or other flavors complement that of a juice or juice combination.

The one or more flavorings may be used in the form of an emulsion. A flavoring emulsion can be prepared by mixing some or all of the flavorings together, optionally together with other ingredients of the food or beverage, and an emulsifying agent. The emulsifying agent can be added with or after the flavorings mixed together. In certain exemplary embodiments the emulsifying agent is water-soluble. Exemplary suitable emulsifying agents include gum acacia, modified starch, carboxymethylcellulose, gum tragacanth, gum ghatti and other suitable gums. Additional suitable emulsifying agents will be apparent to those skilled in the art of beverage formulations, given the benefit of this disclosure. The emulsifier in exemplary embodiments comprises greater than about 3% of the mixture of flavorings and emulsifier. In certain exemplary embodiments the emulsifier is from about 5% to about 30% of the mixture.

Carbon dioxide can be used to provide effervescence to certain exemplary embodiments of the beverages disclosed here. Any of the techniques and carbonating equipment known in the art for carbonating beverages can be employed. Carbon dioxide can enhance beverage taste and appearance and may aid in safeguarding the beverage purity by inhibiting and/or destroying objectionable bacteria. In certain embodiments, for example, the beverage can have a $CO_2$ level up to about 4.0 volumes carbon dioxide. Other embodiments can have, for example, from about 0.5 to about 5.0 volumes of carbon dioxide. As used herein, one volume of carbon dioxide refers to the amount of carbon dioxide absorbed by a given quantity of a given liquid, such as water, at 60° F. (16° C.) and one atmospheric pressure. A volume of gas occupies the same space as does the liquid by which it is dissolved. The carbon dioxide content can be selected by those skilled in the art based on the desired level of effervescence and the impact of the carbon dioxide on the taste or mouthfeel of the beverage.

In certain embodiments, caffeine can be added to any of the disclosed foods, beverages, or syrups described herein. The amount of caffeine added can be determined by the desired properties of a given food, beverage, or syrup, and any applicable regulatory provisions of the country where the food, beverage, or syrup is marketed. In certain embodiments caffeine can be included in an amount sufficient to provide a final beverage product having less than about 0.02 weight percent caffeine. The caffeine must be of purity acceptable for use in foods and beverages. The caffeine may be natural or synthetic in origin.

The food and beverage products disclosed here can contain additional ingredients, including, generally, any of those typically found in food and beverage formulations. Examples of such additional ingredients include, but are not limited to, caramel and other coloring agents or dyes, foaming or antifoaming agents, gums, emulsifiers, tea solids, cloud components, and mineral and non-mineral nutritional supplements. Examples of non-mineral nutritional supplement ingredients are known to those of ordinary skill in the art and include, for example, antioxidants and vitamins, including Vitamins A, D, E (tocopherol), C (ascorbic acid), B (thiamine), B2 (riboflavin), B6, B12, K, niacin, folic acid, biotin, and combinations thereof. The optional non-mineral nutritional supplements are typically present in amounts generally accepted under good manufacturing practices. Exemplary amounts can be between about 1% and about 100% Recommended Daily Value (RDV), where such RDVs are established. In certain exemplary embodiments the non-mineral nutritional supplement ingredient(s) can be present in an amount of from about 5% to about 20% RDV, where established.

Preservatives may be used in at least certain embodiments of the food products and beverages disclosed here. That is, at least certain exemplary embodiments can contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the product at any suitable time during production, e.g., in some cases prior to the addition of the sweetener composition. As used here, the terms "preservation system" or "preservatives" include all suitable preservatives approved for use in food and beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives may be used in amounts not exceeding mandated maximum levels under applicable laws and regulations.

In the case of beverages in particular, the level of preservative used can be adjusted according to the planned final product pH and/or the microbiological spoilage potential of the particular beverage formulation. The maximum level employed typically is about 0.05 weight percent of the beverage. It will be within the ability of those skilled in the art, given the benefit of this disclosure, to select a suitable preservative or combination of preservatives for beverages according to this disclosure.

Other methods of preservation suitable for at least certain exemplary embodiments of the products disclosed here include, e.g., aseptic packaging and/or heat treatment or thermal processing steps, such as hot filling and tunnel pasteurization. Such steps can be used to reduce yeast, mold and microbial growth in the beverage products. For example, U.S. Pat. No. 4,830,862 discloses the use of pasteurization in the production of fruit juice beverages as well as the use of suitable preservatives in carbonated beverages. U.S. Pat. No. 4,925,686 discloses a heat-pasteurized freezable fruit juice composition which contains sodium benzoate and potassium sorbate. Both of these patents are incorporated by reference in their entireties. In general, heat treatment includes hot fill methods typically using high temperatures for a short time, e.g., about 190° F. for 10 seconds, tunnel pasteurization methods typically using lower temperatures for a longer time, e.g., about 160° F. for 10-15 minutes, and retort methods typically using, e.g., about 250° F. for 3-5 minutes at elevated pressure, i.e., at pressure above 1 atmosphere.

Suitable antioxidants may be selected from the group consisting of rutin, quercetin, flavonones, flavones, dihydroflavonols, flavonols, flavandiols, leucoanthocyanidins, flavonol glycosides, flavonone glycosides, isoflavonoids, and neoflavonoids. In particular, the flavonoids may be, but not limited to, quercetin, eriocitrin, neoeriocitrin, narirutin, naringin, hesperidin, hesperetin, neohesperidin, neoponcirin, poncirin, rutin, isorhoifolin, rhoifolin, diosmin, neodiosmin, sinensetin, nobiletin, tangeritin, catechin, catechin gallate, epigallocatechin, epigallocatechin gallate, oolong tea polymerized polyphenol, anthocyanin, heptamethoxyflavone, daidzin, daidzein, biochaminn A, prunetin, genistin, glycitein, glycitin, genistein, 6,7,4' trihydroxy isoflavone, morin, apigenin, vitexin, balcalein, apiin, cupressuflavone, datiscetin, diosmetin, fisetin, galangin, gossypetin, geraldol, hinokiflavone, primuletin, pratol, luteolin, myricetin, orientin, robinetin, quercetagetin, and hydroxy-4-flavone.

Suitable food grade acids are water soluble organic acids and their salts and include, for example, phosphoric acid, sorbic acid, ascorbic acid, benzoic acid, citric acid, tartaric acid, propionic acid, butyric acid, acetic acid, succinic acid, glutaric acid, maleic acid, malic acid, valeric acid, caproic acid, malonic acid, aconitic acid, potassium sorbate, sodium benzoate, sodium citrate, amino acids, and combinations of any of them. Such acids are suitable for adjusting the pH of the beverage.

Suitable food grade bases are sodium hydroxide, potassium hydroxide, and calcium hydroxide. Such bases also are suitable for adjusting the pH of a beverage.

Food products that can contain the sweetener composition include, but are not limited to cereal grains such as oatmeal, cream of wheat, and the like, dairy foods such as yogurt, pudding, and the like, snack bars such as granola bars, as well as baked goods and baking mixes, breakfast cereals, cheeses, chewing gum, condiments, relishes, salad dressings, confections and frostings, dairy product substitutes, fats and oils, frozen dairy desserts and mixes, fruit and water ices, gelatins, and fillings, gravies and sauces, pet foods, hard candy and cough drops, jams and jellies, processed fruits and fruit juices, processed vegetables and vegetable juices, snack foods, soft candy, soups and soup mixes, sauces, toppings, and syrups, baby food, baby formula, coffee whiteners, crackers, egg products, reconstituted vegetables, and oral pharmaceutical dosage forms. The sweetener composition can further be utilized in beverage powders.

EXAMPLES

The formulations and compositions described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

General Tasting Procedure: Unless otherwise specified in a given example, tastings were performed by a single taster using a "sip, spit, rinse" protocol. Under this protocol, the taster:
a. sipped up to about 10 ml of a given solution and assessed the sweetness, mouthfeel, and other characteristics of the solution during its residence in the taster's mouth;
b. spit out the solution after making the assessment; and
c. rinsed with water to cleanse the palate before testing any further samples.

Example 1

Reference solutions: 5%, 7%, and 9% aqueous sucrose (sugar) solutions were prepared. Variant solution: A 5% aqueous sucrose solution containing 400 ppm phloroglucinol was also prepared. Lab taste results: The variant solution was sweeter than 5% aqueous sucrose solution and very similar to 7% aqueous sucrose solution.

Example 2

Reference solutions: 5%, 7%, and 9% aqueous sucrose solutions were prepared as in Example 1. Variant solution: A 5% aqueous sucrose solution containing 800 ppm of phloroglucinol was also prepared. Lab taste results: The variant solution was sweeter than the 7% aqueous sucrose solution but not as sweet as the 9% aqueous sucrose solution. The temporal seemed different. Sweetness of the control came out right away whereas sweetness of the variant took a split of a second to show but the backend seemed even sweeter. However, the sweet taste was clean without lingering.

Example 3

Reference solutions: 5%, 7%, 8% and 9% sucrose solutions in aqueous pH 3.0 citrate buffer solutions (citric acid 2.26 g plus trisodium citrate 0.32 g in 2 L water) were prepared. Variant solution: A 5% aqueous sucrose solution was prepared with 800 ppm of phloroglucinol in the absence of citrate buffer. Lab taste results: The sweetness of the variant solution was close to 8% sucrose. The temporal seemed different. Sweetness of the control came out right away whereas sweetness of the variant took a split of a second to show but the backend seemed even sweeter. However, the sweet taste was clean without lingering.

Example 4

Reference solutions: 2.5%, 3.5%, and 4% aqueous fructose (Sigma) solutions were prepared. Variant solution: A 2.5% aqueous fructose solution including 800 ppm of phloroglucinol was also prepared. Lab taste results: The variant solution was sweeter than 3.5% aqueous fructose solution and close to the sweetness of the 4% aqueous fructose solution, especially at the backend. The 4% aqueous fructose solution had more front end but the variant solution was sweeter in backend.

Example 5

Reference solutions: 5%, 7%, 8% and 9% aqueous glucose (Sigma) solutions were prepared. Variant solution: A 5% aqueous glucose solution containing 800 ppm phloroglucinol was also prepared. Lab taste results: The variant solution was about the same sweetness as the 8% aqueous glucose solution, but not quite as sweet as the 9% aqueous glucose solution. The temporal effect of the variant solution was similar to the temporal effect of the 8% aqueous glucose solution.

Example 6

Reference solutions: 5%, 6%, 7%, 8% and 9% aqueous sucrose solutions were prepared. Variant solutions: 5% aqueous sucrose solution containing phloroglucinol at 40 ppm, 100 ppm, 200 ppm, 400 ppm, 600 ppm, and 800 ppm were also prepared. The variants were then tasted and assessed for their similarity to the reference solutions. The results of the ranking are shown graphically in FIG. 1, and show an approximately linear correlation between phloroglucinol concentration and apparent sweetness.

Example 7

Reference solutions: 8%, 9%, 10%, and 11% aqueous sucrose solutions were prepared. Variant solution: An 8% aqueous sucrose solution containing 800 ppm of phloroglucinol was also prepared. Lab taste results: The variant solution imparted a higher sweetness than 10% aqueous sucrose solution and about the same as the 11% aqueous sucrose solution especially at the backend.

Example 8

Reference solutions: 250 ppm and 320 ppm aqueous rebaudioside A solutions were prepared. Variant solution: A 250 ppm aqueous rebaudioside A solution including 250 ppm of phloroglucinol was also prepared. Lab taste results: The variant solution had sweetness similar to 320 ppm rebaudioside A solution and a sweeter backend. The bitter aftertaste of rebaudioside A was not changed.

Example 9

Compositions were prepared and tasted to see if phloroglucinol tastes sweet at concentrations ranging from 300 ppm to 800 ppm. No sweet taste was observed.

| Phloroglucinol concentration in water | 300 ppm | 400 ppm | 500 ppm | 600 ppm | 800 ppm |
|---|---|---|---|---|---|
| Taste | No taste | No taste | No taste | No taste | No taste |

Example 10

A 5% aqueous sucrose solution including 800 ppm phloroglucinol as in Example 2 was tasted by a second taster who observed that the taste was close to an 8% aqueous sucrose solution. An 8% aqueous sucrose solution containing 800 ppm phloroglucinol as in Example 7 was also tasted by the second taster and was observed to be sweeter than an 11% aqueous sucrose solution. The second taster further observed that a 250 ppm rebaudioside A solution with 800 ppm phloroglucinol as in Example 8 had sweetness similar to a 320 ppm rebaudioside A solution. The bitterness of the variant solution did not change in the presence of phloroglucinol.

Example 11

A third taster tasted the 8% and 11% aqueous sucrose reference solutions described in Example 10 and the variant solution (8% sucrose with 800 ppm phloroglucinol) and observed that that the variant solution was slightly sweeter than that of 11% aqueous sucrose solution.

Example 12

Sources: A bottle of cola concentrate (HFCS-55) and a bottle of concentrate having ⅓ less HFCS (the "Brix-reduced syrup") were obtained. An appropriate volume of the Brix-reduced syrup was combined with phloroglucinol, via mechanical stirring, to give a Brix-reduced syrup having a phloroglucinol concentration of 4800 ppm. Both concentrates were then used to make cola beverages (volume 4.5 carbonated water) in a 1 plus 5 throw manner. The finished variant cola beverage contained 800 ppm of phloroglucinol. The control (11.3 Brix) and variant beverages were tasted and the sweetness of the two was equal, despite the fact that the sweetness of the variant cola without phloroglucinol was only 8 Brix. In addition, the variant imparted good mouthfeel. However, the variant seemed more sour but with less caramel sweet flavor. After being stored at 90° F. for 18 days, lab taste comparison showed the sweetness remained about the same but the flavor difference between the control and variant after storage at 90° F. was significantly less noticeable.

Example 13

800 ppm phloroglucinol was added to half can of SIERRA MIST. This variant was much sweeter than the control (untreated half can) with good body. Sourness was about the same.

Example 14

Sugar was added to unsweetened QUAKER Instant Oatmeal (IQO) Original flavor. A high sugar control comprising 8 g sugar per bag of IQO (29 g) was prepared. A low sugar control comprising 5 g sugar per bag of IQO (29 g) was also prepared. A variant formulation comprising 5 g sugar and 137 mg of phloroglucinol per bag of IQO was also prepared.

The high control, low control, and variant formulations were placed in individual beakers and combined with about 200 mL of hot water. The resulting mixtures were stirred and then tasted. Taste tests were conducted while the mixtures were still warm and after the mixtures had cooled to room temperature. The variant, at both temperatures, tasted sweeter than the low control but not quite as sweet as the high control.

Example 15

Tests were conducted to determine whether phloroglucinol enhanced the saltiness of sodium chloride. Unexpectedly, salt rendered the taste of phloroglucinol slightly sweet. To analyze this effect, an experiment was conducted to determine whether NaCl could be used as a supplemental sweetness enhancer.

A solution of 1 liter of 8% sugar water plus 300 ppm of phloroglucinol was prepared. Half remained as a low control. Salt (300 ppm) was added to the other half (the "variant"). An 11% sugar solution was prepared as a high control. The variant tasted much sweeter than the low control, but not quite as sweet as the high control.

A further 200 ppm of phloroglucinol was added to the variant giving a solution having 8% sugar, 500 ppm phloroglucinol, and 300 ppm salt to become variant 2. Variant 2 tasted the same as the 11% sugar high control.

As noted in Examples 10 and 11, 800 ppm phloroglucinol was required to achieve the sweetness of an 11% sugar solution. This example, however, shows that salt acts as a supplemental sweetness enhancer allowing for a reduction in phloroglucinol concentration from 800 ppm to 500 ppm in the presence of 300 ppm salt.

Example 16

As noted in Example 10, phloroglucinol in water at up to 800 ppm does not have any taste. 100 or 400 ppm salt (sodium chloride) was added to various aqueous phloroglucinol concentrations to see if a sweet taste was imparted to the aqueous phloroglucinol solutions.

| Phloroglucinol concentration in water | 400 ppm | 500 ppm | 600 ppm | 800 ppm |
|---|---|---|---|---|
| Salt in water | 100 ppm | 100 ppm | 100 ppm | 100 ppm |
| Taste | No taste | No taste | No taste | Barely detectable sweetness, if any |
| Phloroglucinol concentration in water | 400 ppm | 500 ppm | 600 ppm | 800 ppm |
| Salt in water | 400 ppm | 400 ppm | 400 ppm | 400 ppm |
| Taste | Barely detectable sweetness | Barely detectable sweetness | Very slightly sweet taste. Estimate ~1% sugar | Very slightly sweet taste. Estimate between 1 and 2% sugar |

Combination of phloroglucinol, salt, and 5% sugar, compared with 8% sugar control.

| Phloroglucinol concentration in water | 400 ppm | 500 ppm | 600 ppm | 800 ppm |
|---|---|---|---|---|
| Salt in water | 400 ppm | 400 ppm | 400 ppm | 400 ppm |
| Sugar in water | 5% | 5% | 5% | 5% |
| Taste | About same as the 8% sugar control, also more body | Same as the 8% sugar control, also more body | Equal or more sweet than the 8% sugar control, more body | Sweeter than the 8% sugar control and more body |

Example 17

Six aqueous solutions of various amounts of phloroglucinol, salt, and sugar were prepared and compared for their sweet taste.

| Phloroglucinol concentration in water | — | 800 ppm | 800 ppm | 600 ppm | — | — |
|---|---|---|---|---|---|---|
| Salt in water | — | — | 400 ppm | 600 ppm | — | — |
| Sugar in water | 8% | 8% | 8% | 8% | 11% | 12% |
| Taste | | Sweet taste is about 11% sugar | Sweet taste is more than 11%, close to 12%. Similar body as 12% sugar | Sweet taste is close to or more than 11%. Similar body as 11% sugar | | |

The addition of 400 ppm salt to the 8% sugar solution with 800 ppm of phloroglucinol increased the sweetness enhancement from 11% sugar equivalent sweetness to that of 12%, and with high body. Since a small concentration of salt is not known to enhance the sweetness of sugar, it can be deduced that the small amount of salt enhances the ability of phloroglucinol to enhance the sweetness of sugar. This is an unexpected phenomenon. A blend of phloroglucinol and small amount of salt can reduce the usage of sugar without losing its good sweet taste.

Example 18

Three tasters conducted taste experiments on the blends identified in the table, below.

| | Solution # | | | | |
|---|---|---|---|---|---|
| | 1 | 2 | 3 | 4 | 5 |
| Sugar | 8% | 8% | 8% | 8% | 11% |
| Phloroglucinol | 0 | 800 ppm | 400 ppm | 200 ppm | 0 |
| D-Psicose | 0 | 0 | 0.5% | 0.5% | 0 |
| Erythritol | 0 | 0 | 0 | 0.5% | 0 |

Taste Results:
Taster 1: Solution #2 had the same sweetness intensity as solution #5, while solutions #3 and #4 were slightly less sweet than solution #5, but had cleaner sweetness profiles.
Taster 2: Solutions #2 and #4 were sweeter than solution #5. Solution #3 had the same sweetness as solution #5 while solutions #3 and #4 had better mouthfeel than solution 5
Taster 3: Solutions #2 and 3 were sweeter than solution #5. Solution 3 had good mouthfeel. Solution #4 was about as sweet as solution #5, but was syrupy and its flavor lingered.

Example 18A

Solutions comprising sugar, phloroglucinol, D-psicose, and erythritol, (solutions A, B, C, and D in the table below), were screened by 5 testers for sweetness in comparison to control sugar solutions 1 and 5.

|  | Solution # | | | | | |
|---|---|---|---|---|---|---|
|  | 1 | A | B | C | D | 5 |
| Sugar | 8% | 8% | 8% | 8% | 8% | 11% |
| Phloroglucinol | 0 | 600 ppm | 600 ppm | 500 ppm | 400 ppm | 0 |
| D-Psicose | 0 | 1% | 1% | 1% | 1% | 0 |
| Erythritol | 0 | 0 | 0.5% | 0 | 0 | 0 |

Taste Results:

Taster 1: Solutions A, C, and D were all very sweet and the sweetness was close to that of solution #5. Solution B was sweeter than solution #5. Solutions A, B, C, and D all had clean sweetness and good mouthfeel.

Taster 2: Solutions A, C, and D had sweetness close to that of solution #5. Solution B was sweeter than solution #5. Solutions A, B, C, and D all had good mouthfeel.

Taster 3: Solution A was slightly less sweet than solution #5, but was very clean. Solution B was much sweeter than solution #5. The sweetness disappeared quickly (no lingering). Solution C was also much sweeter than solution #5, but had good mouthfeel. Solution D was sweeter than solution #5 and seemed syrupy.

These results showed that increased amounts of D-psicose (alone and in combination with erythritol) permitted a decrease in phloroglucinol concentration when compared with the formulations used in Example 18. For example, Solution #2 in Example 18 required 800 ppm phloroglucinol to achieve sweetness similar to the high control. But in this example, phloroglucinol concentration could be reduced to 600 or 500 ppm while providing sweetness greater than the 11% sugar high control.

Example 19

Experiments were conducted on a sugar reduced cola beverage. A control bottle of cola concentrate (HFCS-55) and a bottle of Brix reduced variant concentrate having 35% less HFCS than the control were used. The Brix reduced syrup was made into variant cola concentrate by mixing it with 2400 ppm phloroglucinol and 6% D-psicose with mechanical stirring. Both concentrates were then used to make cola beverages with volume 4.5 carbonated water in a 1 plus 5 throw manner. The finished variant cola beverage contained 400 ppm phloroglucinol and 1% D-psicose.

The control (11.3 Brix) and variant (7.5 Brix not including the presence of phloroglucinol or D-psicose) beverages were tasted and the sweetness of the two was equal. In addition, the variant imparted very good mouthfeel.

Example 20

Taste experiments were conducted for a diet cola beverage. Unsweetened diet cola concentrate was used. Control syrup 1 was made by adding 3000 ppm aspartame to the concentrate. Control syrup 2 was made by adding 2400 ppm rebaudioside M to the diet cola concentrate. Variant syrup 1 was made by adding into the unsweetened diet cola concentrate 1920 ppm rebaudioside M and 4800 ppm of phloroglucinol. Variant syrup 2 was made by adding 1800 ppm rebaudioside M, 3600 ppm phloroglucinol, 6% D-psicose, and 3% erythritol to the unsweetened diet cola concentrate. All concentrates were then used to make diet cola beverages with volume 4.5 carbonated water in a 1 plus 5 throw manner.

The finished control diet cola beverage 1 contained 500 ppm aspartame. The finished control diet cola beverage 2 contained 400 ppm rebaudioside M. The finished diet cola beverage variant 1 contained 320 ppm rebaudioside M and 800 ppm phloroglucinol. The finished diet cola beverage variant 2 contained 300 ppm rebaudioside M, 600 ppm phloroglucinol, 1% D-psicose, and 0.5% of erythritol.

A total of 5 diet cola tasters evaluated the four beverages. The consensus was that the diet cola variant 1 had very good sweetness and similar taste profile as the aspartame control. The testers further stated that Variant 1 was sweeter than the rebaudioside M control 2. Diet cola variant 2 was unanimously judged far sweeter than both controls.

Example 21

The high and low controls described in Example 14 were again prepared. A variant formulation comprising 5 g sugar, 100 mg phloroglucinol, and 1 g of D-psicose per bag of IQO (29 g) was also prepared. The high control, low control, and variant formulations were placed in individual beakers and combined with about 200 mL of hot water. The resulting mixtures were stirred and then tasted. Tasting was performed while the IQO was warm and after the IQO cooled to room temperature. According to the tester, the variant IQO had a sweetness similar to the high control.

Example 22

Experiments were conducted utilizing phloroglucinol and rebaudioside C in a sugar solutions.

|  | Solution 1 | Solution 2 | Solution 3 | Solution 4 | Solution 5 |
|---|---|---|---|---|---|
| Sugar | 8% | 8% | 8% | 8% | 11% |
| Phloroglucinol |  | 500 ppm |  | 500 ppm |  |
| Rebaudioside C |  |  | 350 ppm | 350 ppm |  |

Two testers tasted each of solutions 1 through 5, in the table above. Both solutions #2 and #3 tasted sweeter than solution 1. Solution #4 imparted a significant higher degree of sweetness approximately equal to solution #5. Surprisingly, the quality of solution #4 was very sugary; even more so than with solution #2 or solution #3 alone. Combination of phloroglucinol with rebaudioside C therefore appears to be synergistic, providing a better result than either compound by itself.

Example 23

Taste experiments were conducted with sugar solutions comprising phloroglucinol and one of rebaudioside B, rebaudioside M, and trilobatin as set forth in the table, below.

| | Solution 1 | Solution 2 | Solution 3 | Solution 4 | Solution 5 |
|---|---|---|---|---|---|
| Sugar | 8% | 8% | 8% | 8% | 11% |
| Phloro-glucinol | 500 ppm | 500 ppm | 500 ppm | 500 ppm | |
| Other enhancer | | rebaudioside B 200 ppm* | rebaudioside M 10 ppm | trilobatin 100 ppm | |

Two testers tasted these solutions. According to the panelists, solution #4 was sweeter than, and had a "sugary quality" not present in, solutions without trilobatin. Solution #2 was sweeter and more sugary than a solution without rebaudioside B, but solution #2 was translucent, not transparent. Solution #3 was not sweeter than the control.

Example 24

Five aqueous solutions comprising sugar, phloroglucinol, and/or rubusoside were prepared as set forth in the table below and tested for sweetness.

| | Control | Solution 1 | Solution 2 | Solution 3 | Solution 4 |
|---|---|---|---|---|---|
| Sugar | 8% | 8% | 8% | 8% | 0% |
| Phloroglucinol | | 500 ppm | | 500 ppm | |
| Rubusoside* | | | 100 ppm | 100 ppm | 100 ppm |
| Water | 0.5 L | 0.5 L | 0.5 L | 0.5 L | 0.5 L |

Rubusoside 70% purity was isolated from Guang Xi sweet tea, supplied by Jin Tan Natural Products Company Solution 1 was determined to be sweeter than the control, while solution 2 was not distinguishable from the control. Solution 3, however, was sweeter than the control and was more sugar like with more body and a quick onset than solution 1. Solution 4 was not sweet.

Example 25

Four sample solutions were presented to 15 trained sensory discrimination panelists: 5% sucrose, 7% sucrose, 9% sucrose and a test sample comprising 5% sucrose and 400 ppm phloroglucinol. Panelists were asked to rank the samples in order of sweet taste intensity from low sweet to high sweet. Each panelist tasted each sample twice during the study such that each sample was judged a total of 30 times.

| Sample | Mean rank | Group* |
|---|---|---|
| 9% sucrose | 4.0 | a |
| 7% sucrose | 2.67 | b |
| 5% sucrose + 400 ppm phloroglucinol | 2.17 | b |
| 5% sucrose | 1.17 | c |

*Assignment to a different group, i.e. a, b, or c, indicates that a statistically significant difference (p ≤ 0.05) in sweetness was observed using Tukey's Multiple Comparison test. Samples in the same group did not have statistically significant sweetness differences.

Figure 2:
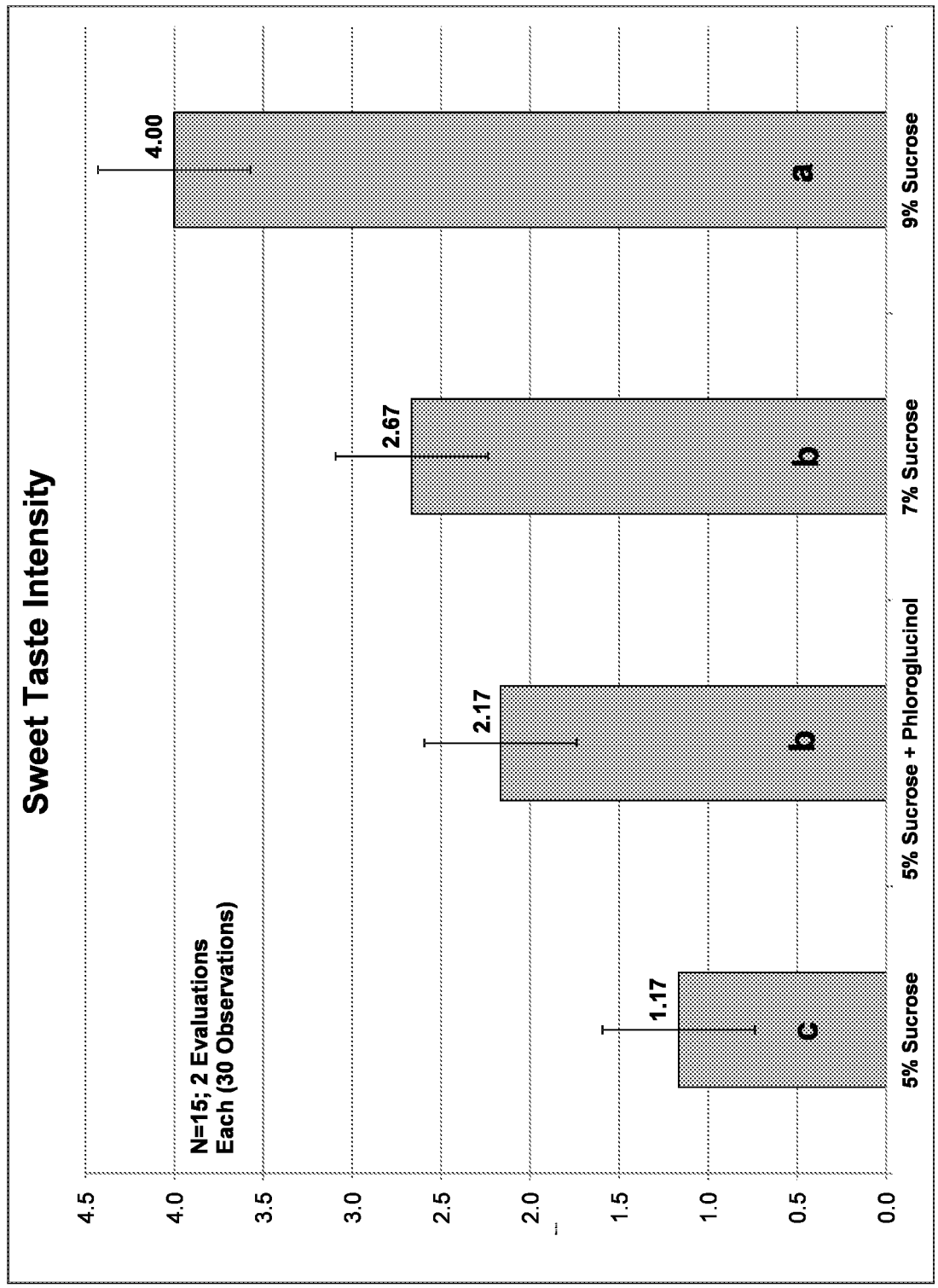
FIG. 2 depicts the sweetness enhancement observed in a sucrose solution comprising a known quantity of phloroglucinol compared to sucrose solutions not containing phloroglucinol.

According to this experiment, phloroglucinol (400 ppm) increased the sweet taste of a 5% sucrose solution to approximately 6.4%—an approximately 28% enhancement. These results are also shown graphically in FIG. 2.

Example 26

15 trained sensory discrimination panelists were presented with four sample solutions: 5% sucrose, 7% sucrose, 9% sucrose, and a test sample comprising 5% sucrose, 400 ppm phloroglucinol, and 200 ppm sodium chloride. Panelists were asked to rank the samples in order of sweet taste intensity from low sweet to high sweet. Each panelist tasted each sample twice during the study such that each sample was judged a total of 30 times.

The results are summarized in the following table.

| Sample | Mean rank | Group* |
|---|---|---|
| 9% sucrose | 3.97 | a |
| 7% sucrose | 2.57 | b |
| 5% sucrose + 400 ppm phloroglucinol + 200 ppm sodium chloride | 2.27 | b |
| 5% sucrose | 1.20 | c |

*Assignment to a different group, i.e. a, b, or c, indicates that a statistically significant difference (p ≤ 0.05) in sweetness was observed using Tukey's Multiple Comparison test. Samples in the same group did not have statistically significant sweetness differences.

Figure 3:
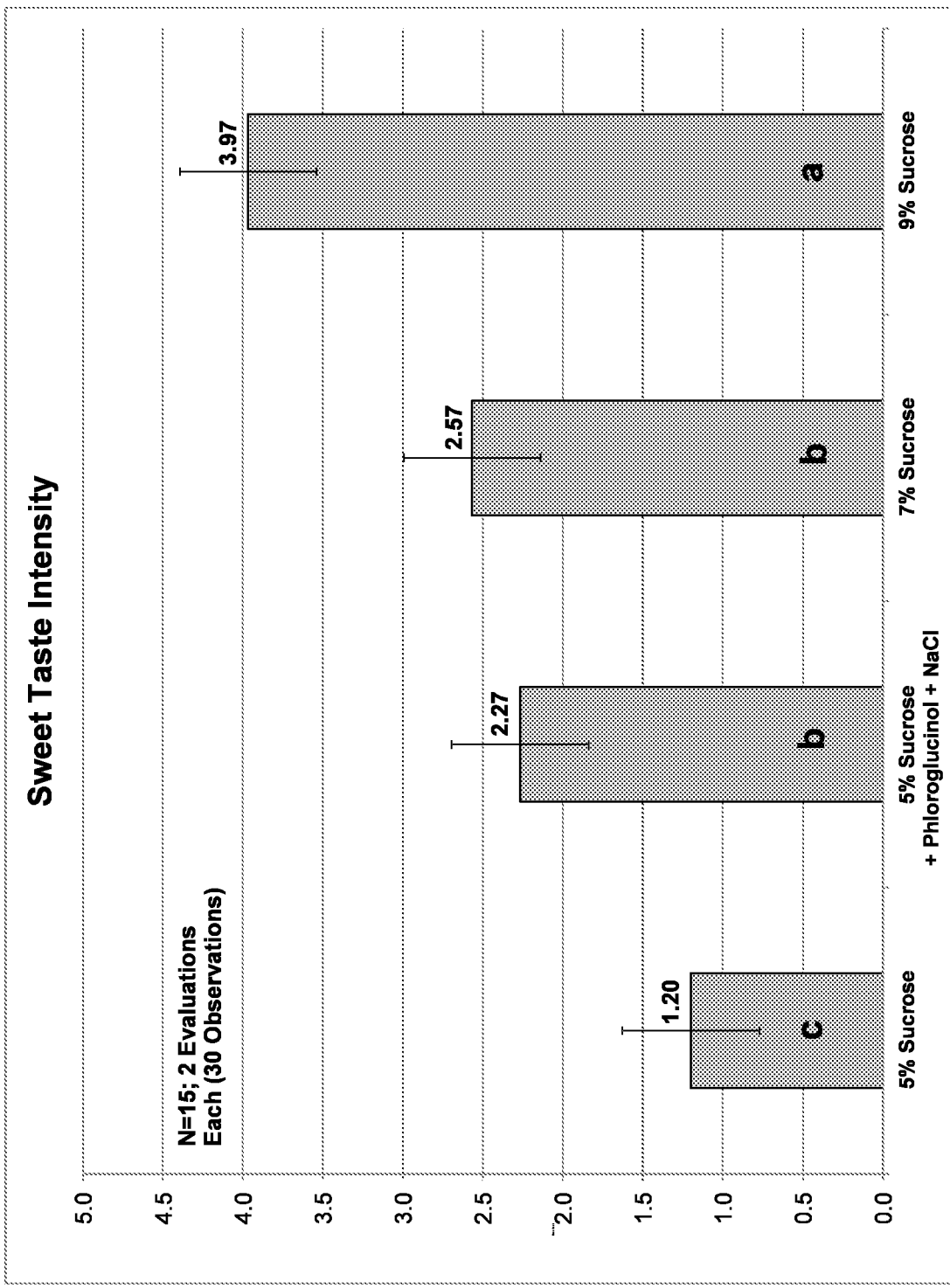
FIG. 3 depicts the sweetness enhancement observed in a sucrose solution comprising a known quantity of phloroglucinol and salt, compared to sucrose solutions not containing phloroglucinol and salt.

According to this experiment, phloroglucinol (400 ppm) and sodium chloride (200 ppm) increased the sweet taste of a 5% sucrose solution to approximately 6.6%—an approximately 32% enhancement. These results are also shown graphically in FIG. 3.

Example 27

Figure 4:
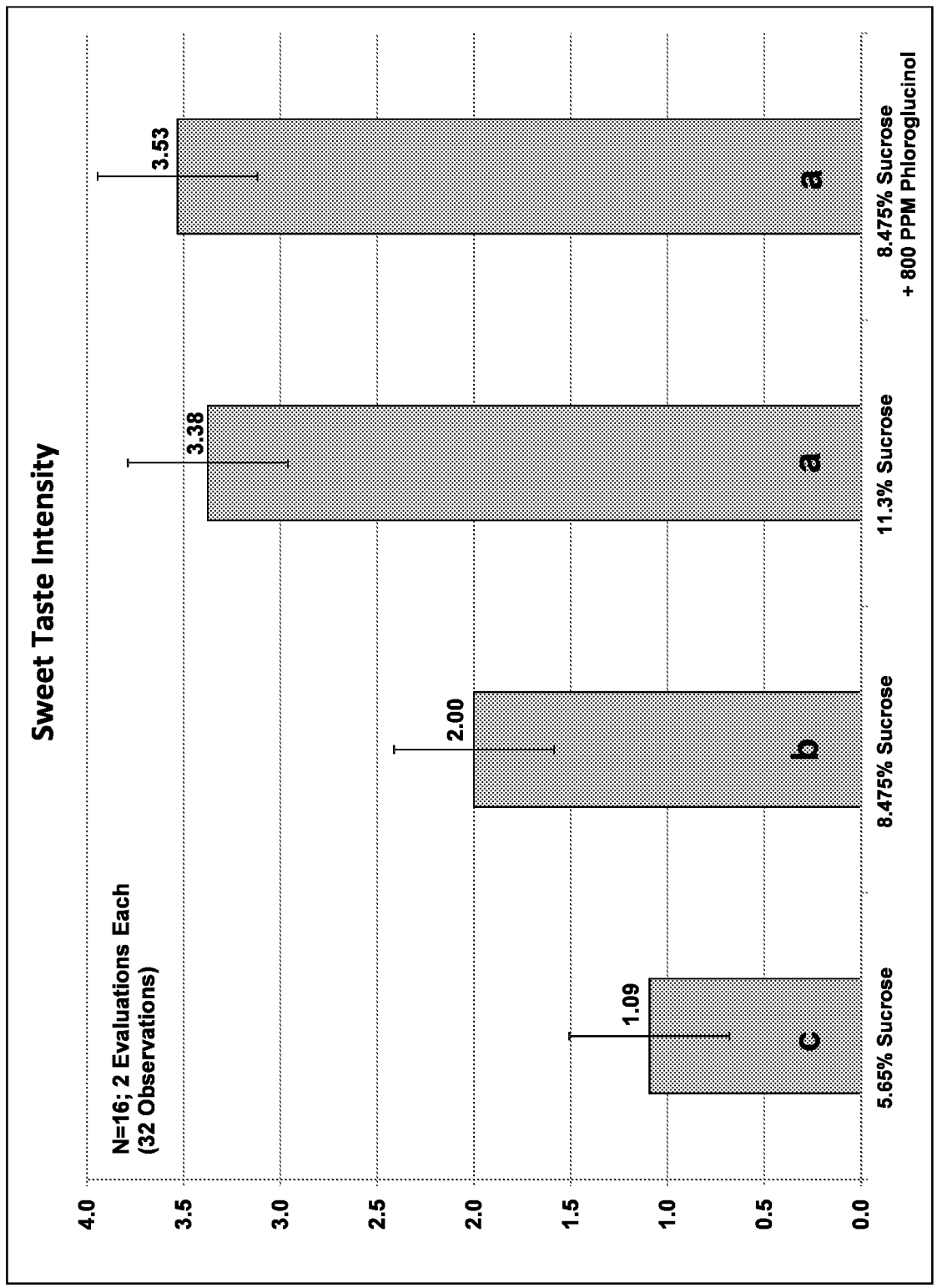
FIG. 4 depicts the sweetness enhancement observed in a sucrose solution comprising a known quantity of phloroglucinol compared to sucrose solutions not containing phloroglucinol.

Four sample solutions were presented to 16 trained sensory discrimination panelists: 5.65% sucrose, 8.475% sucrose, 11.3% sucrose, and the test sample (8.475% sucrose plus 800 ppm phloroglucinol). Panelists were asked to rank the samples in order of sweet taste intensity from low sweet to high sweet. Each panelist was presented a replicate set to render a total of 32 judgment data points. The results are summarized in the following table and shown in FIG. 4.

| Sample | Mean rank | Group* |
|---|---|---|
| 8.475% sucrose + 800 ppm phloroglucinol | 3.53 | a |
| 11.3% sucrose | 3.38 | a |
| 8.475% sucrose | 2.00 | b |
| 5.65% sucrose | 1.09 | c |

*Assignment to a different group, i.e. a, b, or c, indicates that a statistically significant difference (p ≤ 0.05) in sweetness was observed using Tukey's Multiple Comparison test. Samples in the same group did not have statistically significant sweetness differences.

Thus, according to the expert tasters, phloroglucinol (800 ppm) increased the sweet taste of an 8.475% sucrose solution to approximately 11.76% (about 39% enhancement), ranking it sweeter than an 11.3% solution in an absolute sense, but statistically indistinguishable from the 11.3% solution.

While this disclosure mentions specific examples and embodiments, those skilled in the art will appreciate that there are numerous variations and modifications within the spirit and scope of the disclosure as set forth in the appended claims.

What is claimed is:

1. A sweetener composition comprising at least one nutritive sweetener or natural non-nutritive sweetener, and a compound of Formula I:

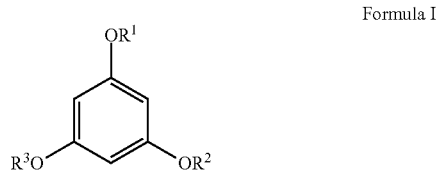

Formula I in an amount sufficient to increase the sweetness intensity of the at least one nutritive sweetener or natural non-nutritive sweetener, wherein:

each of $R^1$, $R^2$, and $R^3$ is independently selected from the group consisting of H, $C_1$-$C_3$ alkane, glucosyl, and —C(=O)$R^4$;

wherein each $R^4$ is independently methyl or ethyl; and wherein at least one of $R^1$, $R^2$, and $R^3$ is $C_1$-$C_3$ alkane, glucosyl, or —C(=O)$R^4$.

2. The sweetener composition of claim 1, wherein each of $R^1$, $R^2$, and $R^3$ is $CH_3$.

3. The sweetener composition of claim 1, further comprising at least one supplemental sweetness enhancer in an amount sufficient to further enhance the sweetness of the at least one sweetener but in an amount below the supplemental sweetness enhancer's sweetness recognition threshold concentration.

4. The sweetener composition of claim 3, wherein the supplemental sweetness enhancer is D-psicose, erythritol, rubusoside, rebaudioside B, rebaudioside C, trilobatin, phyllodulcin, brazzein, mogrosides, or a combination of any of the foregoing.

5. The sweetener composition of claim 1, wherein the sweetener is a nutritive sweetener.

6. The sweetener composition of claim 5, wherein the compound of Formula I and the nutritive sweetener are present in a weight ratio of from about 1:150 to about 1:50.

7. The sweetener composition of claim 1, wherein the sweetener is a natural non-nutritive sweetener.

8. The sweetener composition of claim 7, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

9. The sweetener composition of claim 8, wherein the compound of Formula I and natural non-nutritive sweetener are present in a weight ratio of from about 1.2:1 to about 1:1.2.

10. The sweetener composition of claim 1, wherein the concentration of the compound of Formula I in the sweetener composition is from about 40 to about 1000 ppm.

11. The sweetener composition of claim 5, wherein the nutritive sweetener is selected from the group consisting of sucrose, fructose, glucose, and combinations thereof.

12. The sweetener composition of claim 5, wherein the nutritive sweetener is present at a concentration of from about 1% to about 20% by weight of the composition.

13. The sweetener composition of claim 1, further comprising at least one salt.

14. The sweetener composition of claim 3, wherein the supplemental sweetness enhancer is a rare sugar and wherein the rare sugar is present at a concentration of at least about 1.2 weight percent to about 12 weight percent of the sweetener composition.

15. A food product comprising the composition of claim 1.

16. The food product of claim 15, wherein the food product is selected from the group consisting of cereal, snack bars, dairy products, oatmeal, granola bars, and yogurt.

17. The sweetener composition of claim 1, wherein at least one of $R^1$, $R^2$, or $R^3$ is glucosyl.

18. The sweetener composition of claim 1, further comprising water.

19. A beverage comprising water and the sweetener composition of claim 1.

20. The beverage of claim 19, wherein the amount of nutritive or natural non-nutritive sweetener in the beverage is at least about 25% by weight less relative to a full calorie beverage comprising the same sweetener but lacking the compound of Formula I, wherein the beverage comprising the compound of Formula I has a sweetness equivalent to the full calorie beverage lacking the compound of Formula I when sweetness is measured by a trained sensory discrimination panelist.

* * * * *